United States Patent
Shaver et al.

(10) Patent No.: US 9,458,077 B2
(45) Date of Patent: *Oct. 4, 2016

(54) REDUCING HYDROGEN IODIDE CONTENT IN CARBONYLATION PROCESSES

(71) Applicant: Celanese International Corporation, Irving, TX (US)

(72) Inventors: Ronald D. Shaver, Houston, TX (US); Yaw-Hwa Liu, Missouri City, TX (US); Mark O. Scates, Houston, TX (US)

(73) Assignee: CELANESE INTERNATIONAL CORPORATION, Irving, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/873,651

(22) Filed: Oct. 2, 2015

(65) Prior Publication Data

US 2016/0137574 A1    May 19, 2016

Related U.S. Application Data

(63) Continuation-in-part of application No. 14/694,883, filed on Apr. 23, 2015, now Pat. No. 9,233,907.

(60) Provisional application No. 62/079,961, filed on Nov. 14, 2014.

(51) Int. Cl.
| | |
|---|---|
| *C07C 51/12* | (2006.01) |
| *C07C 51/43* | (2006.01) |
| *C07C 51/44* | (2006.01) |

(52) U.S. Cl.
CPC .............. *C07C 51/12* (2013.01); *C07C 51/43* (2013.01); *C07C 51/44* (2013.01)

(58) Field of Classification Search
CPC .............................. C07C 51/12; C07C 51/47
USPC ................................. 562/519, 608
See application file for complete search history.

(56) References Cited

U.S. PATENT DOCUMENTS

| | | |
|---|---|---|
| 3,769,329 A | 10/1973 | Paulik et al. |
| 5,001,259 A | 3/1991 | Smith et al. |
| 5,026,908 A | 6/1991 | Smith et al. |
| 5,144,068 A | 9/1992 | Smith et al. |
| 5,917,089 A | 6/1999 | Howard |
| 6,339,171 B1 | 1/2002 | Singh et al. |
| 7,678,940 B2 | 3/2010 | Miura et al. |
| 8,168,822 B2 | 5/2012 | Scates et al. |
| 8,318,977 B2 | 11/2012 | Zinobile et al. |
| 8,394,988 B2 | 3/2013 | Torrence et al. |
| 8,940,932 B2 | 1/2015 | Shimizu |
| 8,957,248 B2 | 2/2015 | Miura et al. |
| 9,073,843 B2 | 7/2015 | Shimizu et al. |
| 9,115,071 B2 | 8/2015 | Shimizu et al. |
| 2012/0090981 A1 | 4/2012 | Torrence et al. |
| 2013/0116470 A1 | 5/2013 | Miura et al. |
| 2013/0264186 A1 | 10/2013 | Shimizu et al. |
| 2013/0281735 A1 | 10/2013 | Shimizu et al. |
| 2015/0299084 A1 | 10/2015 | Shimizu et al. |

FOREIGN PATENT DOCUMENTS

| | | |
|---|---|---|
| JP | 2004-300072 A | 10/2004 |
| JP | 2012-532867 A | 12/2012 |
| WO | 99/50218 A1 | 10/1999 |
| WO | 2013/137236 A1 | 9/2013 |
| WO | 2014-097867 A1 | 6/2014 |
| WO | 2014/115826 A1 | 7/2014 |

OTHER PUBLICATIONS

Notice of Allowance mailed on Aug. 19, 2015 for U.S. Appl. No. 14/694,883, 7 pages.
International Search Report dated Jan. 21, 2016 issued in PCT/US2015/0653682.
Jones, J.H., "The Cativa™ Process for the Manufacture of Acetic Acid", Platinum Metals Review, 2002, 44 (3): 94-105.
Office Action received in the corresponding Japanese Patent Application No. 2015-222667, dated Feb. 29, 2016.

*Primary Examiner* — Sikarl Witherspoon
(74) *Attorney, Agent, or Firm* — Kilpatrick Townsend & Stockton LLP

(57) ABSTRACT

Processes for producing acetic acid wherein at least one process vent stream is treated in an absorber column that utilizes a scrubber solvent, e.g., acetic acid, methanol, and/or methyl acetate to remove hydrogen iodide therefrom.

29 Claims, 3 Drawing Sheets

REDUCING HYDROGEN IODIDE CONTENT IN CARBONYLATION PROCESSES

CROSS-REFERENCES TO RELATED APPLICATIONS

This patent application is a continuation-in-part of U.S. Non-Provisional patent application Ser. No. 14/694,883, filed Apr. 23, 2015, which claims priority to U.S. Provisional Patent Application No. 62/079,961, filed Nov. 14, 2014, the disclosure of these applications are incorporated herein by reference in their entireties.

FIELD OF THE INVENTION

This invention relates to processes for producing acetic acid and, in particular, to improved processes for producing acetic acid that effectively reduce hydrogen iodide content in various process streams.

BACKGROUND OF THE INVENTION

A widely used and successful commercial process for synthesizing acetic acid involves the catalyzed carbonylation of methanol, e.g., a methanol (feed) composition, with carbon monoxide. The catalyst may contain rhodium and/or iridium and a halogen promoter, typically methyl iodide. The reaction is conducted by continuously bubbling carbon monoxide through a liquid reaction medium in which the catalyst is dissolved. The reaction medium comprises acetic acid, methyl acetate, water, methyl iodide and the catalyst. The methanol and the carbon monoxide come into contact in the reaction medium and react with one another to form crude acetic acid. Conventional commercial processes for the carbonylation of methanol include those described in U.S. Pat. Nos. 3,769,329, 5,001,259, 5,026,908, and 5,144,068, the entireties of which are incorporated herein by reference. Another conventional methanol carbonylation process includes the Cativa™ process, which is discussed in Jones, J. H. (2002), "The Cativa™ Process for the Manufacture of Acetic Acid," Platinum Metals Review, 44 (3): 94-105, the entirety of which is incorporated herein by reference.

The carbonylation reaction forms reaction by-products such as water, (residual) methyl iodide, and carbonyl impurities, e.g., acetaldehyde. These by-products are typically separated and/or recycled within the system. Hydrogen iodide is another undesirable component that may be present in the reaction medium. The presence of hydrogen iodide in the reaction system is particularly troublesome because it acts as a corrosion agent that may cause metallurgical problems throughout the reaction and separation zones. Thus, the need exists for reducing the formation of hydrogen iodide in carbonylation processes.

US Patent Application Publication No. 2013/0116470 discloses a production process of acetic acid comprising a reaction step for continuously allowing at least one member selected from the group consisting of methanol, dimethyl ether, and methyl acetate to react with carbon monoxide in a catalyst system comprising a rhodium catalyst, an iodide salt, and methyl iodide in the presence of acetic acid and water in a plant compromising a reactor; a flasher; and a distillation column; wherein part of the vaporized stream is introduced into a heat exchanger. The process achieves a production of acetic acid with a high purity in a resource-saving and energy-saving equipment by efficiently removing a reaction heat even in a large-sized plant.

U.S. Pat. No. 8,318,977 discloses a methanol carbonylation system including an absorber tower adapted for receiving a vent gas stream and removing methyl iodide therefrom with a scrubber solvent, the absorber tower being coupled to first and second extractant sources, which are capable of supplying different first and second extractants. A switching system including valves alternatively provides first or second extractants to the absorber tower and returns the used solvent and absorbed material to the carbonylation system to accommodate different operating modes. This reference does not mention hydrogen iodide.

While the above-described processes provide general processes for purifying a crude acetic acid product, these processes fail to specifically address the separation of hydrogen iodide from the crude product. The need exists for improved processes for producing acetic acid that provide for separation and removal of hydrogen iodide from a crude acetic acid product.

SUMMARY OF THE INVENTION

This invention relates to processes producing acetic acid, the processes comprising the steps of carbonylating, in a reactor, at least one of methanol, dimethyl ether, and methyl acetate in a reaction medium comprising a metal catalyst, methyl iodide, an iodide salt, and optionally acetic acid and a finite amount water, to form a crude acetic acid product comprising acetic acid and optionally venting from the reactor a reactor vent stream comprising hydrogen iodide and directing the reactor vent stream to the absorber tower. The processes further comprise the steps of flashing the crude acetic acid product, with or without heat, to form a first vapor stream comprising acetic acid and methyl iodide (and optionally hydrogen iodide) and a first liquid residue stream comprising metal catalyst and halide salt and optionally condensing at least a portion of the first vapor stream to form a flasher vent stream comprising hydrogen iodide and directing the flasher vent stream to the absorber tower. The process further comprise the step of separating, in a light ends column, the first vapor stream to form a second vapor stream comprising methyl iodide and hydrogen iodide, a side draw comprising purified acetic acid product, and a second liquid residue stream. The second vapor stream may be decanted to form a decanter vent stream comprising hydrogen iodide and the at least a portion of the second vapor stream may comprise the decanter vent stream. The separating further may further comprise condensing at least a portion of the second vapor stream to form a light ends vent stream comprising hydrogen iodide and directing the light ends vent stream to an absorber tower. The processes further comprise the steps of feeding to the absorber tower at least a portion of at least one of the reactor vent stream, the flasher vent stream, and the second vapor stream; contacting the absorber tower feed with a first absorbent comprising acetic acid to absorb methyl iodide and to form a first absorber return stream comprising the first absorbent and the absorbed methyl iodide; conveying the first absorber return stream to the light ends column and/or drying column; and terminating the supply of first absorbent to the absorber tower. The processes further comprise the steps of contacting the absorber tower feed with a second absorbent comprising methanol and/or methyl acetate to absorb methyl iodide and hydrogen iodide and to form a second absorber return stream comprising the second absorbent and the absorbed methyl iodide; and conveying the second absorber return stream to the reactor. The process may further comprise the step of chilling the first absorbent and/or the second absorbent prior to the respective contacting. The process may further comprise the step of mixing the second absorber return stream with methanol or a reactive derivative thereof prior to the conveying. In one embodiment, the absorber tower feed comprises methyl acetate and the first and second absorbents absorb methyl acetate from the absorber tower feed. In one embodiment, the process does not employ a stripper column to treat the first absorbent and/or the second absorbent. The carbonylating may be conducted while maintaining the reaction system at concentrations of 2 to 25% by weight iodide salt, 1 to 20% by weight methyl iodide, 0.1 to 30% by weight methyl acetate, and 0.1 to 10% by weight water. The second absorber return stream may not be returned to the separation train. The contacting of the absorber tower feed with the methanol or methyl acetate in the second absorbent may form methyl iodide. The conveying of the second absorber return stream may comprise the steps of conveying the second absorber return stream to the reactor during a transition period; following the transition period, continuing to feed the second absorber return stream to the reactor; and conveying the second absorber return stream to the reactor after the termination of the supply of first absorbent. The second vapor stream further comprises volatile components.

The invention also relates to processes for operating an absorber tower in a carbonylation process comprising the steps of carbonylating, in a reactor, at least one of methanol, dimethyl ether, and methyl acetate in a reaction medium comprising a metal catalyst, methyl iodide, an iodide salt, and optionally acetic acid and a finite amount water, to form a crude acetic acid product comprising acetic acid and optionally venting from the reactor a reactor vent stream comprising hydrogen iodide and directing the reactor vent stream to the absorber tower. The processes further comprise the steps of flashing the crude acetic acid product, with or without heat, to form a first vapor stream comprising acetic acid and methyl iodide (and optionally hydrogen iodide) and a first liquid residue stream comprising metal catalyst and halide salt and optionally condensing at least a portion of the first vapor stream to form a flasher vent stream comprising hydrogen iodide and directing the flasher vent stream to the absorber tower. The process further comprise the step of separating, in a light ends column, the first vapor stream to form a second vapor stream comprising methyl iodide and hydrogen iodide, a side draw comprising purified acetic acid product, and a second liquid residue stream. The second vapor stream may be decanted to form a decanter vent stream comprising hydrogen iodide and the at least a portion of the second vapor stream may comprise the decanter vent stream. The separating further may further comprise condensing at least a portion of the second vapor stream to form a light ends vent stream comprising hydrogen iodide and directing the light ends vent stream to an absorber tower. The process may further comprise the step of feeding to an absorber tower at least a portion of at least one of the reactor vent stream, the flasher vent stream, and the second vapor stream to initiate a start-up period and, during the start-up period, contacting the absorber tower feed with a first absorbent comprising acetic acid to absorb methyl iodide and to form a first absorber return stream comprising the first absorbent and the absorbed methyl iodide; conveying the first absorber return stream to the light ends column and/or drying column; transitioning from start up to steady operation during a changeover period by terminating the supply of first absorbent to the absorber tower. The process further comprises the step of providing to the absorber tower a second absorbent comprising methanol and/or methyl acetate, wherein, during at least a portion of the changeover period, acetic acid, methanol and methyl iodide are provided to the absorber tower; forming a combined absorber return stream comprising acetic acid, methanol, and methyl iodide; conveying the combined absorber return stream from the absorber tower to the reactor; initiating steady state operation after the changeover period, and, during steady state operation, contacting the second vapor stream with the second absorbent to absorb methyl iodide, hydrogen iodide to form a second absorber return stream comprising the second absorbent and the absorbed methyl iodide. The processes further comprise the steps of during the steady state operation, mixing the second absorber return stream with methanol or a reactive derivative thereof to form a mixed stream; and conveying the mixed stream to the reactor. The processes may further comprise the step of chilling the first absorbent and/or the second absorbent prior to the respective contacting. The termination of supply of first absorbent to the absorber tower and provision of the second absorbent to the absorber tower may occur substantially simultaneously.

The invention also relates to a process comprising the steps of: carbonylating, in a reactor, at least one of methanol, dimethyl ether, and methyl acetate in a reaction medium comprising a metal catalyst, methyl iodide, an iodide salt, and optionally acetic acid and a finite amount water, to form a crude acetic acid product comprising acetic acid; optionally venting from the reactor a reactor vent stream comprising hydrogen iodide; condensing at least a portion of the reactor vent stream to form a condensed reactor vent stream; feeding to an absorber tower an absorber tower feed comprising at least a portion of the condensed reactor vent stream; contacting the absorber tower feed with a first absorbent selected from the group consisting of acetic acid, methanol, and methyl acetate, preferably acetic acid, to absorb methyl iodide and hydrogen iodide and to form a first extract comprising the first absorbent and the absorbed methyl iodide and hydrogen iodide; conveying the first extract, directly or indirectly, to the light ends column and/or drying column; decreasing the supply of first absorbent to the absorber tower; contacting the absorber tower feed with a second absorbent comprising methanol and/or methyl acetate to absorb methyl iodide and hydrogen iodide and to form a second extract comprising the second absorbent and the absorbed methyl iodide; conveying the second extract, directly or indirectly, to the reactor.

The invention also relates to a process comprising the steps of: carbonylating, in a reactor, at least one of methanol, dimethyl ether, and methyl acetate in a reaction medium comprising a metal catalyst, methyl iodide, an iodide salt, and optionally acetic acid and a finite amount water, to form a crude acetic acid product comprising acetic acid; flashing the crude acetic acid product, with or without heat, to form a first vapor stream comprising acetic acid and methyl iodide and a first liquid residue stream comprising metal catalyst and halide salt, optionally condensing a portion of the first vapor stream to form a condensed flasher return stream and a flasher vent stream comprising hydrogen iodide; feeding to an absorber tower an absorber tower feed comprising at least a portion of the flasher vent stream (or the condensed flasher vent stream); contacting the absorber tower feed with a first absorbent selected from the group consisting of acetic acid, methanol, and methyl acetate, preferably acetic acid, to absorb methyl iodide and hydrogen iodide and to form a first extract comprising the first absorbent and the absorbed methyl iodide and hydrogen iodide; conveying the first extract, directly or indirectly, to the light ends column and/or drying column; decreasing the supply of first absorbent to the absorber tower; contacting the absorber tower feed with a second absorbent comprising methanol and/or methyl acetate to absorb methyl iodide and hydrogen iodide and to form a second extract comprising the second absorbent and the absorbed methyl iodide; conveying the second extract, directly or indirectly, to the reactor.

The invention also relates to a process comprising the steps of: carbonylating, in a reactor, at least one of methanol, dimethyl ether, and methyl acetate in a reaction medium comprising a metal catalyst, methyl iodide, an iodide salt, and optionally acetic acid and a finite amount water, to form a crude acetic acid product comprising acetic acid; flashing the crude acetic acid product, with or without heat, to form a first vapor stream comprising acetic acid and methyl iodide and a first liquid residue stream comprising metal catalyst and halide salt; separating, in a light ends column, the flashed first vapor stream to form a second vapor stream comprising methyl iodide and hydrogen iodide, a side draw comprising purified acetic acid product, and a second liquid residue stream; optionally condensing the second vapor stream, feeding to an absorber tower an absorber tower feed comprising at least a portion of the second vapor stream; contacting the absorber tower feed with a first absorbent selected from the group consisting of acetic acid, methanol, and methyl acetate, preferably acetic acid, to absorb methyl iodide and hydrogen iodide and to form a first extract comprising the first absorbent and the absorbed methyl iodide and hydrogen iodide; conveying the first extract, directly or indirectly, to the light ends column and/or drying column; decreasing the supply of first absorbent to the absorber tower; contacting the absorber tower feed with a second absorbent comprising methanol and/or methyl acetate to absorb methyl iodide and hydrogen iodide and to form a second extract comprising the second absorbent and the absorbed methyl iodide; conveying the second extract, directly or indirectly, to the reactor. Two absorbent steps are employed in this embodiment.

The invention also relates to a process comprising the steps of: carbonylating, in a reactor, at least one of methanol, dimethyl ether, and methyl acetate in a reaction medium comprising a metal catalyst, methyl iodide, an iodide salt, and optionally acetic acid and a finite amount water, to form a crude acetic acid product comprising acetic acid; flashing the crude acetic acid product, with or without heat, to form a first vapor stream comprising acetic acid and methyl iodide and a first liquid residue stream comprising metal catalyst and halide salt, separating, in a light ends column, the flashed first vapor stream to form a second vapor stream comprising methyl iodide and hydrogen iodide, a side draw comprising purified acetic acid product, and a second liquid residue stream; decanting the second vapor stream to form a light phase comprising acetaldehyde and hydrogen iodide and a heavy phase comprising acetaldehyde, methyl iodide, methyl acetate, and hydrogen iodide; separating at least a portion of the light phase and/or the heavy phase to a PRC removal system to form a PRS overhead comprising hydrogen iodide; optionally collecting the PRS overhead in an overhead receiver; optionally venting from the overhead receiver a PRS overhead receiver vent stream comprising hydrogen iodide; feeding to an absorber tower an absorber tower feed comprising at least a portion of the PRS overhead receiver vent stream and/or the PRS overhead; contacting the absorber tower feed with a first absorbent selected from the group consisting of acetic acid, methanol, and methyl acetate, preferably acetic acid, to absorb methyl iodide and hydrogen iodide to form a first extract comprising the first absorbent and the absorbed methyl iodide and hydrogen iodide; decreasing the supply of first absorbent to the absorber tower; contacting the absorber tower feed with a second absorbent comprising methanol and/or methyl acetate to absorb methyl iodide and hydrogen iodide and to form a second extract comprising the second absorbent and the absorbed methyl iodide.

The invention also relates to a process comprising the steps of: carbonylating, in a reactor, at least one of methanol, dimethyl ether, and methyl acetate in a reaction medium comprising a metal catalyst, methyl iodide, an iodide salt, and optionally acetic acid and a finite amount water, to form a crude acetic acid product comprising acetic acid; flashing the crude acetic acid product, with or without heat, to form a first vapor stream comprising acetic acid and methyl iodide and a first liquid residue stream comprising metal catalyst and halide salt, optionally condensing a portion of the first vapor stream to form a condensed flasher return stream and a flasher vent stream comprising hydrogen iodide; separating, in a light ends column, the flashed first vapor stream to form a second vapor stream comprising methyl iodide and hydrogen iodide, a side draw comprising purified acetic acid product, and a second liquid residue stream; decanting the second vapor stream to form a light phase comprising acetaldehyde and hydrogen iodide and a heavy phase comprising acetaldehyde, methyl iodide, methyl acetate, and hydrogen iodide; separating at least a portion of the light phase and/or the heavy phase in a PRC removal system comprising a first column and a second column to obtain a second PRS overhead comprising hydrogen iodide from the second PRC removal column; optionally collecting the second PRS overhead in an overhead receiver and venting from the overhead receiver a second PRS overhead receiver vent stream comprising hydrogen iodide; feeding to an absorber tower an absorber tower feed comprising at least a portion of the second PRS overhead receiver vent stream and/or the second PRS overhead; contacting the absorber tower feed with a first absorbent selected from the group consisting of acetic acid, methanol, and methyl acetate to absorb hydrogen iodide to form a first extract comprising absorbed hydrogen iodide; and optionally contacting the absorber tower feed with a second absorbent comprising methanol and/or methyl acetate to absorb methyl iodide and hydrogen iodide and to form a second extract comprising the second absorbent and the absorbed methyl iodide.

The invention also relates to a process comprising the steps of: carbonylating, in a reactor, at least one of methanol, dimethyl ether, and methyl acetate in a reaction medium comprising a metal catalyst, methyl iodide, an iodide salt, and optionally acetic acid and a finite amount water, to form a crude acetic acid product comprising acetic acid; flashing the crude acetic acid product, with or without heat, to form a first vapor stream comprising acetic acid and methyl iodide and a first liquid residue stream comprising metal catalyst and halide salt, optionally condensing a portion of the first vapor stream to form a condensed flasher return stream and a flasher vent stream comprising hydrogen iodide; separating, in a light ends column, the flashed first vapor stream (or the condensed first vapor stream) to form a second vapor stream comprising methyl iodide and hydrogen iodide, a side draw comprising purified acetic acid product, and a second liquid residue stream; decanting the second vapor stream to form a light phase comprising acetaldehyde and hydrogen iodide and a heavy phase comprising acetaldehyde, methyl iodide, methyl acetate, and hydrogen iodide; separating at least a portion of the light phase and/or the heavy phase in a PRC removal system to form a PRS overhead comprising hydrogen iodide; optionally collecting the PRS overhead in an overhead receiver and optionally venting from the overhead receiver a PRS overhead receiver vent stream comprising hydrogen iodide; feeding to an absorber tower an absorber tower feed comprising at least a portion of the PRS overhead receiver vent stream and/or the PRS overhead; contacting the absorber tower feed with a first absorbent selected from the group consisting of acetic acid, methanol, and methyl acetate, preferably acetic acid, to absorb hydrogen iodide to form a first extract comprising absorbed hydrogen iodide; and optionally conveying the second extract, directly or indirectly, to the reactor.

The invention also relates to a process comprising the steps of: carbonylating, in a reactor, at least one of methanol, dimethyl ether, and methyl acetate in a reaction medium comprising a metal catalyst, methyl iodide, an iodide salt, and optionally acetic acid and a finite amount water, to form a crude acetic acid product comprising acetic acid; flashing the crude acetic acid product, with or without heat, to form a first vapor stream comprising acetic acid and methyl iodide and a first liquid residue stream comprising metal catalyst and halide salt, optionally condensing a portion of the first vapor stream to form a condensed flasher return stream and a flasher vent stream comprising hydrogen iodide; separating, in a light ends column, the flashed first vapor stream to form a second vapor stream comprising methyl iodide and hydrogen iodide, a side draw comprising purified acetic acid product, and a second liquid residue stream; decanting the second vapor stream to form a light phase comprising acetaldehyde and hydrogen iodide and a heavy phase comprising acetaldehyde, methyl iodide, methyl acetate, and hydrogen iodide; separating at least a portion of the light phase and/or the heavy phase in a PRC removal system comprising a single column to form a PRS overhead comprising hydrogen iodide; optionally collecting the PRS overhead in an overhead receiver and venting from the overhead receiver a PRS overhead receiver vent stream comprising hydrogen iodide; feeding to an absorber tower an absorber tower feed comprising at least a portion of the PRS overhead receiver vent stream and/or the PRS overhead; contacting the absorber tower feed with a first absorbent selected from the group consisting of acetic acid, methanol, and methyl acetate to absorb hydrogen iodide to form a first extract comprising absorbed hydrogen iodide; and optionally contacting the absorber tower feed with a second absorbent comprising methanol and/or methyl acetate to absorb methyl iodide and hydrogen iodide and to form a second extract comprising the second absorbent and the absorbed methyl iodide.

The invention also relates to a process comprising the steps of: carbonylating, in a reactor, at least one of methanol, dimethyl ether, and methyl acetate in a reaction medium comprising a metal catalyst, methyl iodide, an iodide salt, and optionally acetic acid and a finite amount water, to form a crude acetic acid product comprising acetic acid; flashing the crude acetic acid product, with or without heat, to form a first vapor stream comprising acetic acid and methyl iodide and a first liquid residue stream comprising metal catalyst and halide salt, optionally condensing a portion of the first vapor stream to form a condensed flasher return stream and a flasher vent stream comprising hydrogen iodide; feeding to an absorber tower an absorber tower feed comprising at least a portion of the flasher vent stream (or the condensed flasher vent stream); contacting the absorber tower feed with a first absorbent selected from the group consisting of acetic acid, methanol, and methyl acetate, preferably acetic acid, to absorb methyl iodide and hydrogen iodide to form a first extract comprising the first absorbent, hydrogen iodide, and methyl iodide.

The invention also relates to a process comprising the steps of: carbonylating, in a reactor, at least one of methanol, dimethyl ether, and methyl acetate in a reaction medium comprising a metal catalyst, methyl iodide, an iodide salt, and optionally acetic acid and a finite amount water, to form a crude acetic acid product comprising acetic acid; flashing the crude acetic acid product, with or without heat, to form a first vapor stream comprising acetic acid and methyl iodide and a first liquid residue stream comprising metal catalyst and halide salt; separating, in a light ends column, the flashed first vapor stream (or the condensed flasher vent stream) to form a second vapor stream comprising methyl iodide and hydrogen iodide, a side draw comprising purified acetic acid product, and a second liquid residue stream; feeding to an absorber tower an absorber tower feed comprising at least a portion of the second vapor stream; contacting the absorber tower feed with a first absorbent selected from the group consisting of acetic acid, methanol, and methyl acetate, preferably acetic acid, to absorb methyl iodide and hydrogen iodide to form a first extract comprising the first absorbent, hydrogen iodide, and methyl iodide.

BRIEF DESCRIPTION OF THE DRAWINGS

The present invention will be better understood in view of the appended non-limiting figures, wherein.

DETAILED DESCRIPTION OF THE INVENTION

Introduction

Figure 1:
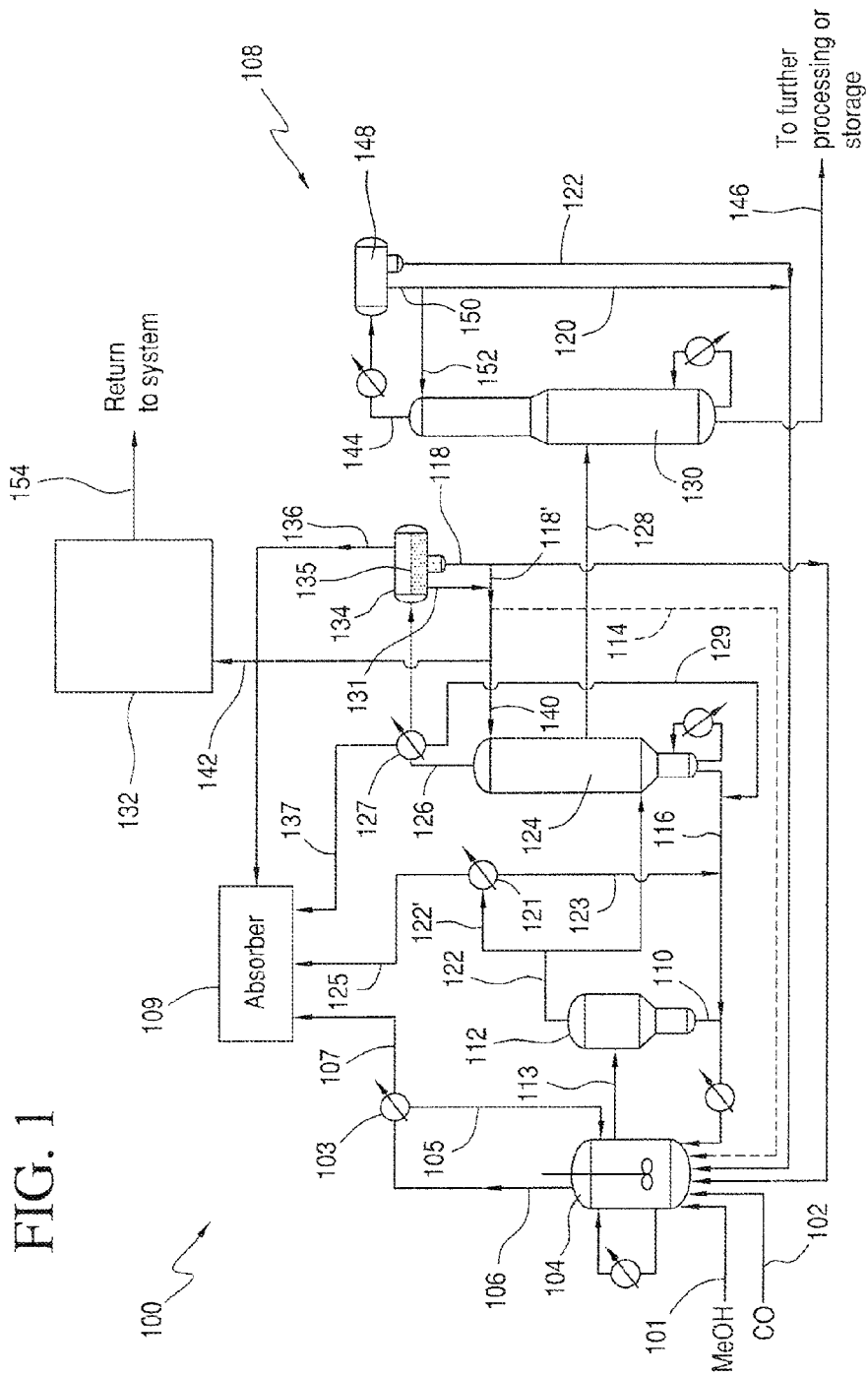
FIG. 1 shows a schematic of an acetic acid production process in accordance with the present invention.

At the outset, it should be noted that in the development of any such actual embodiment, numerous implementation—specific decisions must be made to achieve the developer's specific goals, such as compliance with system related and business related constraints, which will vary from one implementation to another. In addition, the processes disclosed herein can also comprise components other than those cited or specifically referred to, as is apparent to one having average or reasonable skill in the art.

In the summary and this detailed description, each numerical value should be read once as modified by the term "about" (unless already expressly so modified), and then read again as not so modified unless otherwise indicated in context. Also, in the summary and this detailed description, it should be understood that a concentration range listed or described as being useful, suitable, or the like, is intended that any and every concentration within the range, including the end points, is to be considered as having been stated. For example, a range "from 1 to 10" is to be read as indicating each and every possible number along the continuum between about 1 and about 10. Thus, even if specific data points within the range, or even no data points within the range, are explicitly identified or refer to only a few specific data points, it is to be understood that inventors appreciate and understand that any and all data points within the range are to be considered to have been specified, and that inventors possessed knowledge of the entire range and all points within the range.

Throughout the entire specification, including the claims, the following terms have the indicated meanings unless otherwise specified.

As used in the specification and claims, "near" is inclusive of "at." The term "and/or" refers to both the inclusive "and" case and the exclusive "or" case, and is used herein for brevity. For example, a mixture comprising acetic acid and/or methyl acetate may comprise acetic acid alone, methyl acetate alone, or both acetic acid and methyl acetate.

All percentages are expressed as weight percent (wt. %), based on the total weight of the particular stream or composition present, unless otherwise noted. Room temperature is 25° C. and atmospheric pressure is 101.325 kPa unless otherwise noted.

For purposes herein:
acetic acid may be abbreviated as "AcOH";
acetaldehyde may be abbreviated as "AcH";
methyl acetate may be abbreviated "MeAc";
methanol may be abbreviated "MeOH";
methyl iodide may be abbreviated as "MeI";
hydrogen iodide may be abbreviated as "HI";
carbon monoxide may be abbreviated "CO"; and
dimethyl ether may be abbreviated "DME".

HI refers to either molecular hydrogen iodide or dissociated hydriodic acid when at least partially ionized in a polar medium, typically a medium comprising at least some water. Unless otherwise specified, the two are referred to interchangeably. Unless otherwise specified, HI concentration is determined via acid-base titration using a potentiometric end point. In particular, HI concentration is determined via titration with a standard lithium acetate solution to a potentiometric end point. It is to be understood that for purposes herein, the concentration of HI is not determined by subtracting a concentration of iodide assumed to be associated with a measurement of corrosion metals or other non H+ cations from the total ionic iodide present in a sample.

It is to be understood that HI concentration does not refer to iodide ion concentration. HI concentration specifically refers to HI concentration as determined via potentiometric titration.

This subtraction method is an unreliable and imprecise method to determine relatively lower HI concentrations (i.e., less than about 5 weight percent) due to the fact that it assumes all non-H+ cations (such as cations of Fe, Ni, Cr, Mo) are associated with iodide anion exclusively. In reality, a significant portion of the metal cations in this process can be associated with acetate anion. Additionally, many of these metal cations have multiple valence states, which adds even more unreliability to the assumption on the amount of iodide anion which could be associated with these metals. Ultimately, this method gives rise to an unreliable determination of the actual HI concentration, especially in view of the ability to perform a simple titration directly representative of the HI concentration.

For purposes herein, an "overhead" or "distillate" of a distillation column refers to at least one of the lower boiling condensable fractions which exits at or near the top, (e.g., proximate to the top), of the distillation column, and/or the condensed form of that stream or composition. Obviously, all fractions are ultimately condensable, yet for purposes herein, a condensable fraction is condensable under the conditions present in the process as readily understood by one of skill in the art. Examples of noncondensable fractions may include nitrogen, hydrogen, and the like. Likewise, an overhead stream may be taken just below the upper most exit of a distillation column, for example, wherein the lowest boiling fraction is a non-condensable stream or represents a de-minimis stream, as would be readily understood by one of reasonable skill in the art.

The "bottoms" or "residuum" of a distillation column refers to one or more of the highest boiling fractions which exit at or near the bottom of the distillation column, also referred to herein as flowing from the bottom sump of the column. It is to be understood that a residuum may be taken from just above the very bottom exit of a distillation column, for example, wherein the very bottom fraction produced by the column is a salt, an unusable tar, a solid waste product, or a de-minimis stream as would be readily understood by one of reasonable skill in the art.

For purposes herein, distillation columns comprise a distillation zone and a bottom sump zone. The distillation zone includes everything above the bottom sump zone, i.e., between the bottom sump zone and the top of the column. For purposes herein, the bottom sump zone refers to the lower portion of the distillation column in which a liquid reservoir of the higher boiling components is present (e.g., the bottom of a distillation column) from which the bottom or residuum stream flows upon exiting the column. The bottom sump zone may include reboilers, control equipment, and the like.

It is to be understood that the term "passages", "flow paths", "flow conduits", and the like in relation to internal components of a distillation column are used interchangeably to refer to holes, tubes, channels, slits, drains, and the like, which are disposed through and/or which provide a path for liquid and/or vapor to move from one side of the internal component to the other side of the internal component. Examples of passages disposed through a structure such as a liquid distributor of a distillation column include drain holes, drain tubes, drain slits, and the like, which allow a liquid to flow through the structure from one side to another.

Average residence time is defined as the sum total of all liquid volume hold-up for a given phase within a distillation zone divided by the average flow rate of that phase through the distillation zone. The hold-up volume for a given phase can include liquid volume contained in the various internal components of the column including collectors, distributors and the like, as well as liquid contained on trays, within downcomers, and/or within structured or random packed bed sections.

Treatment of Hydrogen Iodide Containing Streams

Some conventional carbonylation reaction mixtures have been found to contain hydrogen iodide, which dissociates in the presence of water causing corrosion within the reaction zone and the separation zone. Hydrogen iodide also creates environmental concerns as well as cost-related concerns. The presence of hydrogen iodide has been recognized in some process streams, e.g., reaction vent streams or flasher vent streams. Although some conventional separation trains do utilize absorbent towers, e.g., to treat methyl iodide, the use of these towers to treat the hydrogen iodide in these streams, e.g., recovery or removal thereof, however, has not been addressed.

It has now been discovered that the hydrogen iodide in many of these streams may be treated using an absorbent (or multiple absorbents). The use of the absorbent effectively removes hydrogen iodide from various process streams, e.g., reactor vents, flasher vents, light ends column vents, and PRC removal system vents. The absorption using appropriate absorbents surprisingly and unexpectedly separates the hydrogen iodide and allows for proper treatment and/or recycling thereof. In particular cases, the inventors have found that the use of a single absorbent is advantageous to treat hydrogen iodide. Preferably, the absorbent comprises acetic acid. The use of a single absorbent allows the resultant extract stream to then be purified by directly conveying the extractant stream back to the separation zone. In some cases, the use of a single absorbent eliminates the need to further treat the resultant extract before returning it back to the separation zone.

Also, conventional systems and literature have not addressed the presence of hydrogen iodide in the overhead streams, bottoms streams, and/or accompanying receivers of a PRC removal system. The inventors have now found that, in some cases, the hydrogen iodide in these overhead streams is significant. Without being bound by theory, it is postulated that the PRC removal process actually produces hydrogen iodide via hydrolysis of methyl iodide. Thus, the amount of hydrogen iodide in the overhead streams and bottoms streams of a PRC removal system become enriched in hydrogen iodide. The higher levels of hydrogen iodide creates and exacerbates the environmental, corrosion, and cost-related concerns mentioned above. The inventors have found that treatment of these streams using an absorbent (or multiple absorbents) surprisingly and effectively provides for effective removal of hydrogen iodide from these streams. For environmental as well as cost-related reasons.

In addition, it has now been discovered that the use of an absorber tower that employs the (alternating) use of multiple scrubber solvents can be used to effectively separate hydrogen iodide from any of several acetic acid production process streams. Exemplary process streams that may be used as the absorber tower feed include a reactor vent stream, a flasher vent stream, a light ends distillate, a PRC removal system overhead (or a vent from an accompanying receiver) and derivatives of these process streams. The specific combination of scrubbing solvents, as described herein, effectively remove hydrogen iodide from the respective process stream advantageously decreasing the corrosive effects thereof. As a result, metallurgical problems throughout the reaction and separation zones are minimized. In addition, it has been surprisingly found that the use of the specific solvents of the present invention may beneficially lead to the formation of additional methyl iodide, which can then be utilized to increase catalyst stability in the reaction zone (or elsewhere). Without being bound by theory, when methanol and/or methyl acetate are used as a scrubbing solvent, e.g., as a second scrubbing solvent, the methanol and/or methyl acetate may react with hydrogen iodide in the various acetic acid production process streams to form the additional methyl iodide. The processes of the present invention improve the purification of the crude acetic acid product by improving hydrogen iodide removal, increasing methyl iodide formation, and beneficially improving overall catalyst stability.

The present invention relates to processes for producing acetic acid comprising the step of carbonylating, in a reactor, at least one of methanol, dimethyl ether, and methyl acetate in a reaction medium comprising a metal catalyst, methyl iodide, an iodide salt, and optionally acetic acid and water, to form a crude acetic acid product. The crude acetic acid product comprises acetic acid. During the carbonylation reaction, a vent stream may be vented from the reactor. The reactor vent stream may comprise hydrogen iodide, carbon monoxide, nitrogen, and other volatile components. The crude acetic acid product is flashed, with or without heat, to form a first vapor stream and a first liquid residue stream. The first vapor stream comprises acetic acid, hydrogen iodide, and optionally methyl iodide. The first liquid residue stream comprises metal catalyst and halide salt and may be recycled to the reactor. The flashed vapor stream (or a portion thereof) is separated in a light ends column to form a second vapor stream, a side draw, and a second liquid residue. The second vapor stream comprises hydrogen iodide and optionally methyl iodide and acetaldehyde. The second vapor stream may further comprise volatile components, e.g., vaporous acetic acid, water, and/or methyl acetate. The side draw comprises purified acetic acid product, which may be subjected to additional purification steps. The second residue stream comprises acetic acid, water, and catalyst and may be recycled to the reactor. The separating in the light ends column may further comprise condensing at least a portion of the second vapor stream to form a light ends vent stream comprising hydrogen iodide.

The processes further comprise the step of feeding to the absorber tower at least a portion of the reactor vent stream, at least a portion of the flasher vent stream, and/or at least a portion of the second vapor stream.

In one embodiment, at least a portion of the reactor vent stream may be fed to the absorber column. A portion of the reactor vent stream may be separated from the reactor vent stream and fed to the absorber. The entire reactor vent stream may be fed to the absorber. In one embodiment, the portion of the reactor vent stream that is fed to the absorber is formed by directing the reactor vent stream to a heat exchanger, e.g., condensing at least a portion of the reactor vent stream, which yields a reactor vent vapor stream and a condensed reactor return stream. The reactor vent vapor stream may comprise hydrogen iodide and may be fed to the absorber tower. The condensed reactor return stream may be recycled to the reactor.

In one embodiment, at least a portion of the first vapor stream may be fed to the absorber column. A portion of the first vapor stream may be separated from the first vapor stream and fed to the absorber. The entire first vapor stream may be fed to the absorber. In one embodiment, the portion of the first vapor stream that is fed to the absorber is formed by directing the first vapor stream to a heat exchanger, e.g., condensing at least a portion of the first vapor stream, which yields a flasher vent vapor stream and a condensed flasher return stream. The flasher vent vapor stream may comprise hydrogen iodide and may be fed to the absorber tower. The condensed flasher return stream may be recycled to the flasher or the reactor.

In one embodiment, at least a portion of the second vapor stream may be fed to the absorber column. A portion of the second vapor stream is separated from the second vapor stream and fed to the absorber. The entire second vapor stream is fed to the absorber. In one embodiment, the portion of the second vapor stream that is fed to the absorber is formed by directing the second vapor stream to a heat exchanger, e.g., condensing at least a portion of the second vapor stream, which yields a light ends vent vapor stream and a condensed light ends return stream. The light ends vent vapor stream may comprise hydrogen iodide and may be fed to the absorber tower. The condensed light ends return stream may be recycled to the light ends column, the flasher, or the reactor.

In one embodiment, at least a portion of the second vapor stream may be decanted to form a decanter vent stream. The decanter vent stream may comprise hydrogen iodide and may be fed to the absorber tower.

In one embodiment, at least a portion of at least two of the reactor vent stream, the flasher vent stream, the second vapor stream, and a PRC removal system vent are combined to form the absorber tower feed. For example, the reactor vent stream, the flasher vent stream, and the second vapor stream may be combined into a combined vent stream and fed to the absorber. As another example, the flasher vent stream, the second vapor stream, and the PRC removal system vent may be combined into a combined vent stream and fed to the absorber. Thus, the absorber tower feed may, in some embodiments, comprise the combined vent stream.

Regardless of which stream is (streams are) sent to the absorber column, the processes further comprise the step of contacting the absorber tower feed with a first absorbent. The first absorbent preferably absorbs methyl iodide from the absorber tower feed to form a first extract, which comprises the first absorbent and the absorbed methyl iodide. The first absorbent may also preferably absorb hydrogen iodide from the absorber tower feed to form the first extract, which comprises the first absorbent and the absorbed hydrogen iodide. The first absorbent may comprise acetic acid, water, or combinations thereof.

The process further comprises the steps of conveying all or a portion of the first extract to the light ends column and/or drying column and terminating the supply of first absorbent to the absorber tower. For example, the flow of the first absorbent to the absorber column may be stopped using a system of valves, as discussed below.

As used herein, the term "terminating" includes a reducing or decreasing the supply of an absorbent.

The processes, in one embodiment, further comprise the step of contacting the absorber tower feed with a second absorbent. The second absorbent may absorb methyl iodide and hydrogen iodide and thus forms a second extract, which comprises the second absorbent and absorbed methyl iodide. The second absorbent may comprise methanol and/or methyl acetate. In one embodiment, the second absorbent consists essentially of methanol. The processes may further comprise the step of conveying all or a portion of the second extract to the reactor. The conveying of the second extract to the reactor may be performed after the termination of the supply of first absorbent. In one embodiment, the contacting of the absorber tower feed with the methanol or methyl acetate in the second absorbent beneficially forms methyl iodide, which can be utilized to increase catalyst stability in the reactor. In one embodiment, the second extract is mixed with methanol or a reactive derivative thereof prior to being conveyed to the reactor. The second extract is returned to the reactor and is not returned to the separation train for further processing. By sending the absorber stream to the reactor, there is no need for a separate stripper column or processing in light ends or drying column which consumes considerable capacity. As such, the burden on the separation zone is beneficially reduced.

In one embodiment, the process comprises the steps of: carbonylating, in a reactor, at least one of methanol, dimethyl ether, and methyl acetate in a reaction medium comprising a metal catalyst, methyl iodide, an iodide salt, and optionally acetic acid and a finite amount water, to form a crude acetic acid product comprising acetic acid; optionally venting from the reactor a reactor vent stream comprising hydrogen iodide; condensing at least a portion of the reactor vent stream to form a condensed reactor vent stream; feeding to an absorber tower an absorber tower feed comprising at least a portion of the condensed reactor vent stream; contacting the absorber tower feed with a first absorbent selected from the group consisting of acetic acid, methanol, and methyl acetate, preferably acetic acid, to absorb methyl iodide and hydrogen iodide and to form a first extract comprising the first absorbent and the absorbed methyl iodide and hydrogen iodide; conveying the first extract, directly or indirectly, to the light ends column and/or drying column; decreasing the supply of first absorbent to the absorber tower; contacting the absorber tower feed with a second absorbent comprising methanol and/or methyl acetate to absorb methyl iodide and hydrogen iodide and to form a second extract comprising the second absorbent and the absorbed methyl iodide; conveying the second extract, directly or indirectly, to the reactor. Thus, two absorbent steps are employed in this embodiment.

In one embodiment, the process comprises the steps of: carbonylating, in a reactor, at least one of methanol, dimethyl ether, and methyl acetate in a reaction medium comprising a metal catalyst, methyl iodide, an iodide salt, and optionally acetic acid and a finite amount water, to form a crude acetic acid product comprising acetic acid; flashing the crude acetic acid product, with or without heat, to form a first vapor stream comprising acetic acid and methyl iodide and a first liquid residue stream comprising metal catalyst and halide salt, optionally condensing a portion of the first vapor stream to form a condensed flasher return stream and a flasher vent stream comprising hydrogen iodide; feeding to an absorber tower an absorber tower feed comprising at least a portion of the flasher vent stream (or the condensed flasher vent stream); contacting the absorber tower feed with a first absorbent selected from the group consisting of acetic acid, methanol, and methyl acetate, preferably acetic acid, to absorb methyl iodide and hydrogen iodide and to form a first extract comprising the first absorbent and the absorbed methyl iodide and hydrogen iodide; conveying the first extract, directly or indirectly, to the light ends column and/or drying column; decreasing the supply of first absorbent to the absorber tower; contacting the absorber tower feed with a second absorbent comprising methanol and/or methyl acetate to absorb methyl iodide and hydrogen iodide and to form a second extract comprising the second absorbent and the absorbed methyl iodide; conveying the second extract, directly or indirectly, to the reactor. Two absorbent steps are employed in this embodiment.

In one embodiment, the process comprises the steps of: carbonylating, in a reactor, at least one of methanol, dimethyl ether, and methyl acetate in a reaction medium comprising a metal catalyst, methyl iodide, an iodide salt, and optionally acetic acid and a finite amount water, to form a crude acetic acid product comprising acetic acid; flashing the crude acetic acid product, with or without heat, to form a first vapor stream comprising acetic acid and methyl iodide and a first liquid residue stream comprising metal catalyst and halide salt; separating, in a light ends column, the flashed first vapor stream to form a second vapor stream comprising methyl iodide and hydrogen iodide, a side draw comprising purified acetic acid product, and a second liquid residue stream; optionally condensing the second vapor stream, feeding to an absorber tower an absorber tower feed comprising at least a portion of the second vapor stream; contacting the absorber tower feed with a first absorbent selected from the group consisting of acetic acid, methanol, and methyl acetate, preferably acetic acid, to absorb methyl iodide and hydrogen iodide and to form a first extract comprising the first absorbent and the absorbed methyl iodide and hydrogen iodide; conveying the first extract, directly or indirectly, to the light ends column and/or drying column; decreasing the supply of first absorbent to the absorber tower; contacting the absorber tower feed with a second absorbent comprising methanol and/or methyl acetate to absorb methyl iodide and hydrogen iodide and to form a second extract comprising the second absorbent and the absorbed methyl iodide; conveying the second extract, directly or indirectly, to the reactor. Two absorbent steps are employed in this embodiment.

In one embodiment, the process comprises the steps of: carbonylating, in a reactor, at least one of methanol, dimethyl ether, and methyl acetate in a reaction medium comprising a metal catalyst, methyl iodide, an iodide salt, and optionally acetic acid and a finite amount water, to form a crude acetic acid product comprising acetic acid; flashing the crude acetic acid product, with or without heat, to form a first vapor stream comprising acetic acid and methyl iodide and a first liquid residue stream comprising metal catalyst and halide salt, separating, in a light ends column, the flashed first vapor stream to form a second vapor stream comprising methyl iodide and hydrogen iodide, a side draw comprising purified acetic acid product, and a second liquid residue stream; decanting the second vapor stream to form a light phase comprising acetaldehyde and hydrogen iodide and a heavy phase comprising acetaldehyde, methyl iodide, methyl acetate, and hydrogen iodide; separating at least a portion of the light phase and/or the heavy phase to a PRC removal system to form a PRS overhead comprising hydrogen iodide; optionally collecting the PRS overhead in an overhead receiver; optionally venting from the overhead receiver a PRS overhead receiver vent stream comprising hydrogen iodide; feeding to an absorber tower an absorber tower feed comprising at least a portion of the PRS overhead receiver vent stream and/or the PRS overhead; contacting the absorber tower feed with a first absorbent selected from the group consisting of acetic acid, methanol, and methyl acetate, preferably acetic acid, to absorb methyl iodide and hydrogen iodide to form a first extract comprising the first absorbent and the absorbed methyl iodide and hydrogen iodide; decreasing the supply of first absorbent to the absorber tower; contacting the absorber tower feed with a second absorbent comprising methanol and/or methyl acetate to absorb methyl iodide and hydrogen iodide and to form a second extract comprising the second absorbent and the absorbed methyl iodide. Two absorbent steps are employed in this embodiment.

In one embodiment, the process comprises the steps of: carbonylating, in a reactor, at least one of methanol, dimethyl ether, and methyl acetate in a reaction medium comprising a metal catalyst, methyl iodide, an iodide salt, and optionally acetic acid and a finite amount water, to form a crude acetic acid product comprising acetic acid; flashing the crude acetic acid product, with or without heat, to form a first vapor stream comprising acetic acid and methyl iodide and a first liquid residue stream comprising metal catalyst and halide salt, optionally condensing a portion of the first vapor stream to form a condensed flasher return stream and a flasher vent stream comprising hydrogen iodide; separating, in a light ends column, the flashed first vapor stream to form a second vapor stream comprising methyl iodide and hydrogen iodide, a side draw comprising purified acetic acid product, and a second liquid residue stream; decanting the second vapor stream to form a light phase comprising acetaldehyde and hydrogen iodide and a heavy phase comprising acetaldehyde, methyl iodide, methyl acetate, and hydrogen iodide; separating at least a portion of the light phase and/or the heavy phase in a PRC removal system comprising a first column and a second column to obtain a second PRS overhead comprising hydrogen iodide from the second PRC removal column; optionally collecting the second PRS overhead in an receiver and venting from the overhead receiver a second PRS overhead receiver vent stream comprising hydrogen iodide; feeding to an absorber tower an absorber tower feed comprising at least a portion of the second PRS overhead receiver vent stream and/or the second PRS overhead; contacting the absorber tower feed with a first absorbent selected from the group consisting of acetic acid, methanol, and methyl acetate to absorb hydrogen iodide to form a first extract comprising absorbed hydrogen iodide; and optionally contacting the absorber tower feed with a second absorbent comprising methanol and/or methyl acetate to absorb methyl iodide and hydrogen iodide and to form a second extract comprising the second absorbent and the absorbed methyl iodide.

Other embodiments that employ a single absorbent are also contemplated.

In one embodiment, the process comprises the steps of: carbonylating, in a reactor, at least one of methanol, dimethyl ether, and methyl acetate in a reaction medium comprising a metal catalyst, methyl iodide, an iodide salt, and optionally acetic acid and a finite amount water, to form a crude acetic acid product comprising acetic acid; flashing the crude acetic acid product, with or without heat, to form a first vapor stream comprising acetic acid and methyl iodide and a first liquid residue stream comprising metal catalyst and halide salt, optionally condensing a portion of the first vapor stream to form a condensed flasher return stream and a flasher vent stream comprising hydrogen iodide; separating, in a light ends column, the flashed first vapor stream (or the condensed first vapor stream) to form a second vapor stream comprising methyl iodide and hydrogen iodide, a side draw comprising purified acetic acid product, and a second liquid residue stream; decanting the second vapor stream to form a light phase comprising acetaldehyde and hydrogen iodide and a heavy phase comprising acetaldehyde, methyl iodide, methyl acetate, and hydrogen iodide; separating at least a portion of the light phase and/or the heavy phase in a PRC removal system to form a PRS overhead comprising hydrogen iodide; optionally collecting the PRS overhead in an overhead receiver and optionally venting from the overhead receiver a PRS overhead receiver vent stream comprising hydrogen iodide; feeding to an absorber tower an absorber tower feed comprising at least a portion of the PRS overhead receiver vent stream and/or the PRS overhead; contacting the absorber tower feed with a first absorbent selected from the group consisting of acetic acid, methanol, and methyl acetate, preferably acetic acid, to absorb hydrogen iodide to form a first extract comprising absorbed hydrogen iodide; and optionally conveying the second extract, directly or indirectly, to the reactor.

In one embodiment, the process comprises the steps of: carbonylating, in a reactor, at least one of methanol, dimethyl ether, and methyl acetate in a reaction medium comprising a metal catalyst, methyl iodide, an iodide salt, and optionally acetic acid and a finite amount water, to form a crude acetic acid product comprising acetic acid; flashing the crude acetic acid product, with or without heat, to form a first vapor stream comprising acetic acid and methyl iodide and a first liquid residue stream comprising metal catalyst and halide salt, optionally condensing a portion of the first vapor stream to form a condensed flasher return stream and a flasher vent stream comprising hydrogen iodide; separating, in a light ends column, the flashed first vapor stream to form a second vapor stream comprising methyl iodide and hydrogen iodide, a side draw comprising purified acetic acid product, and a second liquid residue stream; decanting the second vapor stream to form a light phase comprising acetaldehyde and hydrogen iodide and a heavy phase comprising acetaldehyde, methyl iodide, methyl acetate, and hydrogen iodide; separating at least a portion of the light phase and/or the heavy phase in a PRC removal system comprising a single column to form a PRS overhead comprising hydrogen iodide; optionally collecting the PRS overhead in an overhead receiver and venting from the overhead receiver a PRS overhead receiver vent stream comprising hydrogen iodide; feeding to an absorber tower an absorber tower feed comprising at least a portion of the PRS overhead receiver vent stream and/or the PRS overhead; contacting the absorber tower feed with a first absorbent selected from the group consisting of acetic acid, methanol, and methyl acetate to absorb hydrogen iodide to form a first extract comprising absorbed hydrogen iodide; and optionally contacting the absorber tower feed with a second absorbent comprising methanol and/or methyl acetate to absorb methyl iodide and hydrogen iodide and to form a second extract comprising the second absorbent and the absorbed methyl iodide.

In one embodiment, the process comprises the steps of: carbonylating, in a reactor, at least one of methanol, dimethyl ether, and methyl acetate in a reaction medium comprising a metal catalyst, methyl iodide, an iodide salt, and optionally acetic acid and a finite amount water, to form a crude acetic acid product comprising acetic acid; flashing the crude acetic acid product, with or without heat, to form a first vapor stream comprising acetic acid and methyl iodide and a first liquid residue stream comprising metal catalyst and halide salt, optionally condensing a portion of the first vapor stream to form a condensed flasher return stream and a flasher vent stream comprising hydrogen iodide; feeding to an absorber tower an absorber tower feed comprising at least a portion of the flasher vent stream (or the condensed flasher vent stream); contacting the absorber tower feed with a first absorbent selected from the group consisting of acetic acid, methanol, and methyl acetate, preferably acetic acid, to absorb methyl iodide and hydrogen iodide to form a first extract comprising the first absorbent, hydrogen iodide, and methyl iodide.

In one embodiment, the process comprises the steps of: carbonylating, in a reactor, at least one of methanol, dimethyl ether, and methyl acetate in a reaction medium comprising a metal catalyst, methyl iodide, an iodide salt, and optionally acetic acid and a finite amount water, to form a crude acetic acid product comprising acetic acid; flashing the crude acetic acid product, with or without heat, to form a first vapor stream comprising acetic acid and methyl iodide and a first liquid residue stream comprising metal catalyst and halide salt; separating, in a light ends column, the flashed first vapor stream (or the condensed flasher vent stream) to form a second vapor stream comprising methyl iodide and hydrogen iodide, a side draw comprising purified acetic acid product, and a second liquid residue stream; feeding to an absorber tower an absorber tower feed comprising at least a portion of the second vapor stream; contacting the absorber tower feed with a first absorbent selected from the group consisting of acetic acid, methanol, and methyl acetate, preferably acetic acid, to absorb methyl iodide and hydrogen iodide to form a first extract comprising the first absorbent, hydrogen iodide, and methyl iodide.

In cases where acetic acid is utilized as the single absorbent, the inventors have found that the hydrogen iodide is absorbed particularly well when acetic acid, methanol, and/or methyl acetate are employed. These absorbents have not been shown in the literature to be effective solvents for hydrogen iodide removal.

By treating the hydrogen iodide-containing streams with the absorbent(s) as discussed above, hydrogen iodide is advantageously separated from the respective stream. Once removed, the hydrogen can beneficially be further utilized or disposed of accordingly.

The processes may further comprise the step of chilling the first absorbent and/or the second absorbent prior to contacting second absorbent with the absorber tower feed.

In one embodiment where multiple absorbents are employed, the absorber tower feed comprises methyl acetate and the first and second absorbents absorb methyl acetate from the absorber tower feed. The methyl acetate in the absorber tower feed may be provided by one or more of the reactor vent stream, the flasher vent stream, and the second vapor stream.

The inventors have further found that, advantageously, the use of two scrubbing solvents, as described herein, eliminates the need for treatment of the first absorbent and/or the second absorbent. Instead, these streams can be directed to existing components of the process, e.g., the reactor, the light ends column, or the drying column.

In cases where a reactor vent is taken from the reactor, the resulting stream may be directed to the flasher to stabilize catalyst. Preferably, the reactor vent is directed to the bottom of the flasher to stabilize the catalyst present in the stream exiting the bottom of the flasher.

In one embodiment where multiple absorbents are employed, the absorber tower alternates between using the first absorbent and the second absorbent. In some cases, a transition period exists between the termination of the use of the first absorbent and the beginning of the use of the second absorbent and vice versa. In some cases, the transition period may be less than 20 minutes, e.g., less than 15 minutes, less than 10 minutes, less than 5 minutes, or less than 3 minutes. In one embodiment, acetic acid is used as an absorbent during a unit startup because the acetic acid can be directed to the purification system that has been operating before the reactor is started. Without being bound by theory, it is believed that if methanol were used before the reactor was running, there would be nowhere for the methanol to be subsequently processed. The start-up period using acetic acid lasts for several hours, e.g., less than 15 hours, less than 10 hours, or less than 5 hours. In one embodiment, the conveying of the second absorber return stream comprises the step of conveying the second extract to the reactor during a transition period; and following the transition period, continuing to feed the second absorber return stream to the reactor. In these cases, once the transition has been made to the second absorbent, e.g., methanol, the absorber stream continues to feed to the reactor where the methanol is consumed as reactant and the MeI is returned to the reactor.

In some cases, the processes relate to a process for starting up the reaction system. For example, the feeding to the absorber tower may initiate a start-up period, and during the start-up period the absorber tower feed is contacted with a first absorbent and the first extract is conveyed to the light ends column and/or drying column, as discussed herein. A transition from start up to steady operation may be initiated (during a changeover period) by terminating the supply of first absorbent to the absorber tower. The second absorbent may be provided to the absorber tower. During at least a portion of the changeover period, acetic acid, methanol, and methyl iodide may be provided to the absorber tower, thus forming a combined absorber return stream comprising acetic acid, methanol, and methyl iodide. The combined absorber return stream may be conveyed from the absorber tower to the reactor. Steady state operation may be initiated after the changeover period. During steady state operation, the second vapor stream may be contacted with a second absorbent, as discussed herein. During the steady state operation, the second absorber return stream may be mixed with methanol or a reactive derivative thereof to form a mixed stream, and the mixed stream may be conveyed to the reactor. In one embodiment, termination of supply of first absorbent to the absorber tower and providing of the second absorbent to the absorber tower occur substantially simultaneously, e.g., within less than 1 minute, within less than 5 minutes, or within less than 20 minutes.

Acetic Acid Production Systems

An exemplary acetic acid production process is described below. In the interest of clarity, not all features of an actual implementation are described in this specification. The process description is merely exemplary and is not meant to limit the scope of the invention.

The carbonylation reaction of methanol to acetic acid product may be carried out by contacting the methanol feed with gaseous carbon monoxide bubbled through an acetic acid solvent reaction medium containing the metal catalyst, e.g., rhodium catalyst, a halogen-containing catalyst promoter, e.g., methyl iodide, additional soluble halide salt, e.g., iodide salt such as lithium iodide, and optionally methyl acetate and/or water, at conditions of temperature and pressure suitable to form the carbonylation product.

The catalyst may be a Group VIII metal catalyst, such as rhodium, and a halogen-containing catalyst promoter. A particularly useful process is the low water rhodium-catalyzed carbonylation of methanol to acetic acid as exemplified in U.S. Pat. No. 5,001,259. Other metal catalysts, e.g., iridium-based catalysts, are contemplated as well. Generally, the metal component, e.g., rhodium component, of the catalyst system is believed to be present in the form of a coordination compound of rhodium with a halogen component providing at least one of the ligands of such coordination compound. In addition to the coordination of rhodium and halogen, it is also believed that carbon monoxide will coordinate with rhodium. The rhodium component of the catalyst system may be provided by introducing into the reaction zone rhodium in the form of rhodium metal, rhodium salts such as the oxides, acetates, iodides, carbonates, hydroxides, chlorides, etc., or other compounds that result in the formation of a coordination compound of rhodium in the reaction environment. The metal catalyst, e.g., rhodium catalyst, is, in some embodiments, present in amounts from 200 to 2000 weight parts per million (wppm).

The halogen-containing catalyst promoter of the catalyst system consists of a halogen compound comprising an organic halide. Thus, alkyl, aryl, and substituted alkyl or aryl halides can be used. Preferably, the halogen-containing catalyst promoter is present in the form of an alkyl halide. Even more preferably, the halogen-containing catalyst promoter is present in the form of an alkyl halide in which the alkyl radical corresponds to the alkyl radical of the feed alcohol, which is being carbonylated. Thus, in the carbonylation of methanol to acetic acid, the halide promoter will include methyl halide, and more preferably methyl iodide.

It will be generally recognized that it is the concentration of iodide ion in the catalyst system that is important and not the cation associated with the iodide, and that at a given molar concentration of iodide the nature of the cation is not as significant as the effect of the iodide concentration. Any metal iodide salt, or any iodide salt of any organic cation, or other cations such as those based on amine or phosphine compounds (optionally, ternary or quaternary cations), can be maintained in the reaction medium provided that the salt is sufficiently soluble in the reaction medium to provide the desired level of the iodide. When the iodide is a metal salt, preferably it is an iodide salt of a member of the group consisting of the metals of Group IA and Group IIA of the periodic table as set forth in the "Handbook of Chemistry and Physics" published by CRC Press, Cleveland, Ohio, 2002-03 (83rd edition). In particular, alkali metal iodides are useful, with lithium iodide being particularly suitable. In the low water carbonylation process, the additional iodide ion over and above the iodide ion present as hydrogen iodide is generally present in the catalyst solution in amounts such that the total iodide ion concentration is from 2 to 20 wt. % and the methyl acetate is generally present in amounts from 0.5 to 30 wt. %, and the methyl iodide is generally present in amounts from 5 to 20 wt. %.

In some embodiments, the desired reaction rates are obtained even at low water concentrations by maintaining in the reaction medium an ester of the desired carboxylic acid and an alcohol, desirably the alcohol used in the carbonylation, and an additional iodide ion that is over and above the iodide ion that is present as hydrogen iodide. A desired ester is methyl acetate. It has been found, as described in U.S. Pat. No. 5,001,259, that under low water concentrations, methyl acetate and lithium iodide act as rate promoters only when relatively high concentrations of each of these components are present and that the promotion is higher when both of these components are present simultaneously. The absolute concentration of iodide ion content provided as merely an example, and is not to be interpreted as limiting.

In embodiments, the process for producing acetic acid further includes introducing a lithium compound into the reactor to maintain the concentration of lithium acetate in an amount from 0.3 to 0.7 wt. % in the reaction medium. In embodiments, an amount of the lithium compound is introduced into the reactor to maintain the concentration of hydrogen iodide in an amount from 0.1 to 1.3 wt. % in the reaction medium. In embodiments, the concentration of the rhodium catalyst is maintained in an amount from 200 to 3000 wppm in the reaction medium, the concentration of water is maintained in amount from 0.1 to 4.1 wt. % in the reaction medium, and the concentration of methyl acetate is maintained from 0.6 to 4.1 wt. % in the reaction medium, based on the total weight of the reaction medium present within the carbonylation reactor.

In embodiments, the lithium compound introduced into the reactor is selected from the group consisting of lithium acetate, lithium carboxylates, lithium carbonates, lithium hydroxide, other organic lithium salts, and mixtures thereof. In embodiments, the lithium compound is soluble in the reaction medium. In an embodiment, lithium acetate dihydrate may be used as the source of the lithium compound.

Lithium acetate reacts with hydrogen iodide according to the following equilibrium reaction (I) to form lithium iodide and acetic acid:

$$\text{LiOAc} + \text{HI} \leftrightarrow \text{LiI} + \text{HOAc} \qquad (I)$$

Lithium acetate is thought to provide improved control of hydrogen iodide concentration relative to other acetates, such as methyl acetate, present in the reaction medium. Without being bound by theory, lithium acetate is a conjugate base of acetic acid and thus reactive toward hydrogen iodide via an acid-base reaction. This property is thought to result in an equilibrium of the reaction (I) which favors reaction products over and above that produced by the corresponding equilibrium of methyl acetate and hydrogen iodide. This improved equilibrium is favored by water concentrations of less than 4.1 wt. % in the reaction medium. In addition, the relatively low volatility of lithium acetate compared to methyl acetate allows the lithium acetate to remain in the reaction medium except for volatility losses and small amounts of entrainment into the vapor crude product. In contrast, the relatively high volatility of methyl acetate allows the material to distill into the purification train, rendering methyl acetate more difficult to control. Lithium acetate is much easier to maintain and control in the process at consistent low concentrations of hydrogen iodide. Accordingly, a relatively small amount of lithium acetate may be employed relative to the amount of methyl acetate needed to control hydrogen iodide concentrations in the reaction medium. It has further been discovered that lithium acetate is at least three times more effective than methyl acetate in promoting methyl iodide oxidative addition to the rhodium [I] complex.

In embodiments, the concentration of lithium acetate in the reaction medium is maintained at greater than or equal to 0.3 wt. %, or greater than or equal to 0.35 wt. %, or greater than or equal to 0.4 wt. %, or greater than or equal to 0.45 wt. %, or greater than or equal to 0.5 wt. %, and/or in embodiments, the concentration of lithium acetate in the reaction medium is maintained at less than or equal to 0.7 wt. %, or less than or equal to 0.65 wt. %, or less than or equal to 0.6 wt. %, or less than or equal to 0.55 wt. %.

It has been discovered that an excess of lithium acetate in the reaction medium can adversely affect the other compounds in the reaction medium, leading to decrease productivity. Conversely, it has been discovered that a lithium acetate concentration in the reaction medium below about 0.3 wt. % is unable to maintain the desired hydrogen iodide concentrations in the reaction medium of below 1.3 wt. %.

In embodiments, the lithium compound may be introduced continuously or intermittently into the reaction medium. In embodiments, the lithium compound is introduced during reactor start up. In embodiments, the lithium compound is introduced intermittently to replace entrainment losses.

The reaction medium may also contain impurities that should be controlled to avoid byproduct formation. One impurity in the reaction medium may be ethyl iodide, which is difficult to separate from acetic acid. Applicant has further discovered that the formation of ethyl iodide may be affected by numerous variables, including the concentration of acetaldehyde, ethyl acetate, methyl acetate and methyl iodide in the reaction medium. Additionally, ethanol content in the methanol source, hydrogen partial pressure and hydrogen content in the carbon monoxide source have been discovered to affect ethyl iodide concentration in the reaction medium and, consequently, propionic acid concentration in the final acetic acid product.

In embodiments, the propionic acid concentration in the acetic acid product may further be maintained below 250 wppm by maintaining the ethyl iodide concentration in the reaction medium at less than or equal to 750 wppm without removing propionic acid from the acetic acid product.

In embodiments, the ethyl iodide concentration in the reaction medium and propionic acid in the acetic acid product may be present in a weight ratio from 3:1 to 1:2. In embodiments, the acetaldehyde:ethyl iodide concentration in the reaction medium is maintained at a weight ratio from 2:1 to 20:1.

In embodiments, the ethyl iodide concentration in the reaction medium may be maintained by controlling at least one of the hydrogen partial pressure, the methyl acetate concentration, the methyl iodide concentration, and/or the acetaldehyde concentration in the reaction medium.

In embodiments, the concentration of ethyl iodide in the reaction medium is maintained/controlled to be less than or equal to 750 wppm, or e.g., less than or equal to 650 wppm, or less than or equal to 550 wppm, or less than or equal to 450 wppm, or less than or equal to 350 wppm. In embodiments, the concentration of ethyl iodide in the reaction medium is maintained/controlled at greater than or equal to 1 wppm, or e.g., 5 wppm, or 10 wppm, or 20 wppm, or 25 wppm, and less than or equal to 650 wppm, or e.g., 550 wppm, or 450 wppm, or 350 wppm.

In embodiments, the weight ratio of ethyl iodide in the reaction medium to propionic acid in the acetic acid product may range from 3:1 to 1:2, or e.g., from 5:2 to 1:2, or from 2:1 to 1:2, or from 3:2 to 1:2.

In embodiments, the weight ratio of acetaldehyde to ethyl iodide in the reaction medium may range from 20:1 to 2:1, or e.g., from 15:1 to 2:1 or from 9:1 to 2:1.

In one embodiment, the gaseous purge stream 106 contains low amounts of hydrogen iodide of less than or equal to 1 wt. %, e.g., less than or equal to 0.9 wt. %, less than or equal to 0.8 wt. %, less than or equal to 0.7 wt. %, less than or equal to 0.5 wt. %. Hydrogen iodide in excess of these amounts may increase the duty on the scrubber to prevent hydrogen iodide from being purged.

In one embodiment, a suitable potassium permanganate test is JIS K1351 (2007).

The liquid reaction medium employed may include any solvent compatible with the catalyst system and may include pure alcohols, or mixtures of the alcohol feedstock and/or the desired carboxylic acid and/or esters of these two compounds. A preferred solvent and liquid reaction medium for the low water carbonylation process contains the desired carboxylic acid product. Thus, in the carbonylation of methanol to acetic acid, a preferred solvent system contains acetic acid.

Water is contained in the reaction medium but desirably at low concentrations for achieving sufficient reaction rates. It has previously been taught, e.g., in U.S. Pat. No. 3,769,329, that in rhodium-catalyzed carbonylation reactions, the addition of water exerts a beneficial effect upon the reaction rate. Thus, some commercial operations are commonly run at water concentrations of greater than 14 wt. %. However, in some embodiments, water concentrations of less than or equal to 14 wt. %, e.g., less than or equal to 10 wt. %, less than or equal to 1 wt. % or less than or equal to 0.1 wt. %, may be utilized. In terms of ranges, the reaction medium may comprise water in an amount from 0.1 wt. % to 14 wt. %, e.g., from 0.2 wt. % to 10 wt. %, from 0.25 wt. % to 5 wt. %, or from 0.25 wt. % to 4.1 wt. %, based on the total weight of the reaction medium.

In one embodiment, the carbonylating is conducted while maintaining the reaction system at concentrations of 2 to 25% by weight iodide salt, 1 to 20% by weight methyl iodide, 0.1 to 30% by weight methyl acetate, and 0.1 to 10% by weight water.

Typical reaction temperatures for carbonylation will be from 150 to 250° C., with the temperature range of 180 to 225° C. being a preferred range. The carbon monoxide partial pressure in the reactor can vary widely but is typically from 2 to 30 atmospheres, e.g., from 3 to 10 atmospheres. Because of the partial pressure of by-products and the vapor pressure of the contained liquids, the total reactor pressure will range from 15 to 40 atmospheres.

Exemplary reaction and acetic acid recovery system 100 is shown in FIG. 1. As shown, methanol-containing feed stream 101 and carbon monoxide-containing feed stream 102 are directed to liquid phase carbonylation reactor 104, in which the carbonylation reaction occurs.

Carbonylation reactor 104 is preferably either a stirred vessel or bubble-column type vessel, with or without an agitator, within which the reacting liquid or slurry contents are maintained, preferably automatically, a predetermined level, which preferably remains substantially constant during normal operation. Into carbonylation reactor 104, fresh methanol, carbon monoxide, and sufficient water are continuously introduced as needed to maintain suitable concentrations in the reaction medium.

In a typical carbonylation process, carbon monoxide is continuously introduced into the carbonylation reactor, desirably through a distribution plate below the agitator, which may be used to stir the contents. The gaseous feed preferably is thoroughly dispersed through the reacting liquid by this stirring means. Gaseous purge stream 106 desirably is vented from the reactor 104 to prevent buildup of gaseous by-products and to maintain a set carbon monoxide partial pressure at a given total reactor pressure. The temperature of the reactor may be controlled and the carbon monoxide feed is introduced at a rate sufficient to maintain the desired total reactor pressure. Stream 113 comprising the liquid reaction medium exits reactor 104. At least a portion of gaseous purge stream 106 is directed to heat exchanger 103 where at least a portion of gaseous purge stream 106 is condensed to form condensed reactor return stream 105 and reactor vent vapor stream 107. At least a portion of gaseous purge stream 106, e.g., reactor vent vapor stream 107, is directed to absorber tower 109. Condensed reactor return stream 105 is recycled to reactor 104.

The crude acetic acid product may be purified in separation zone 108 to recover the acetic acid and recycle catalyst solution, methyl iodide, methyl acetate, and other system components within the process. Thus, a recycled catalyst solution, such as stream 110 from flasher 112, and optionally one or more of recycle streams 114, 116, 118, and 120, also are introduced into the reactor 104. Of course, one or more of the recycle streams may be combined prior to being introduced into the reactor. The separation system also preferably controls water and acetic acid content in the carbonylation reactor, as well as throughout the system, and facilitates PRC removal.

The reaction medium is drawn off from the carbonylation reactor 104 at a rate sufficient to maintain a constant level therein and is provided to flasher 112 via stream 113. In flasher 112, the crude product is separated in a flash separation step to obtain a vapor product stream 122 comprising acetic acid and less volatile stream 110 comprising a catalyst-containing solution (predominantly acetic acid containing the rhodium and the iodide salt along with lesser quantities of methyl acetate, methyl iodide, and water), which preferably is recycled to the reactor, as discussed above.

The vapor product stream 122 also comprises methyl iodide, methyl acetate, hydrogen iodide, water, PRC's. Dissolved gases exiting the reactor and entering the flasher comprise a portion of the carbon monoxide and may also contain gaseous by-products such as methane, hydrogen, and carbon dioxide. Such dissolved gases exit the flasher as part of the overhead stream. At least a portion of vapor product stream 122 is directed to heat exchanger 121, via line 122', where the contents of line 122' are condensed to form condensed flasher return stream 123 and flasher vent vapor stream 125. At least a portion of vapor product stream 122, e.g., flasher vent vapor stream 125, is directed to absorber tower 109. Condensed flasher return stream 123 is recycled to reactor 104.

In one embodiment, the vapor product stream comprises acetic acid, methyl iodide, methyl acetate, water, acetaldehyde, and hydrogen iodide. In one embodiment, the vapor product stream comprises acetic acid in an amount from 45 to 75 wt. %, methyl iodide in an amount from 20 to 50 wt. %, methyl acetate in an amount of less than or equal to 9 wt. %, and water in an amount of less than or equal to 15 wt. %, based on the total weight of the vapor product stream. In another embodiment, the vapor product stream comprises acetic acid in an amount from 45 to 75 wt. %, methyl iodide in an amount from 24 to less than 36 wt. %, methyl acetate in an amount of less than or equal to 9 wt. %, and water in an amount of less than or equal to 15 wt. %, based on the total weight of the vapor product stream. More preferably, the vapor product stream comprises acetic acid in an amount from 55 to 75 wt. %, methyl iodide in an amount from 24 to 35 wt. %, methyl acetate in an amount from 0.5 to 8 wt. %, and water in an amount from 0.5 to 14 wt. %. In yet a further preferred embodiment, the vapor product stream comprises acetic acid in an amount from 60 to 70 wt. %, methyl iodide in an amount from 25 to 35 wt. %, methyl acetate in an amount from 0.5 to 6.5 wt. %, and water in an amount from 1 to 8 wt. %. The acetaldehyde concentration in the vapor product stream may be in an amount from 0.005 to 1 wt. %, based on the total weight of the vapor product stream, e.g., from 0.01 to 0.8 wt. %, or from 0.01 to 0.7 wt. %. In some embodiments the acetaldehyde may be present in amounts less than or equal to 0.01 wt. %. The vapor product stream may comprise hydrogen iodide in an amount less than or equal to 1 wt. %, based on the total weight of the vapor product stream, e.g., less than or equal to 0.5 wt. %, or less than or equal to 0.1 wt. %. Hydrogen iodide is preferably present in the vapor product stream. The vapor product stream is preferably substantially free of, i.e., contains less than or equal to 0.0001 wt. %, propionic acid, based on the total weight of the vapor product stream.

The liquid recycle stream comprises acetic acid, the metal catalyst, corrosion metals, as well as other various compounds. In one embodiment, liquid recycle stream comprises acetic acid in an amount from 60 to 90 wt. %, metal catalyst in an amount from 0.01 to 0.5 wt. %; corrosion metals (e.g., nickel, iron and chromium) in a total amount from 10 to 2500 wppm; lithium iodide in an amount from 5 to 20 wt. %; methyl iodide in an amount from 0.5 to 5 wt. %; methyl acetate in an amount from 0.1 to 5 wt. %; water in an amount from 0.1 to 8 wt. %; acetaldehyde in an amount of less than or equal to 1 wt. % (e.g., from 0.0001 to 1 wt. % acetaldehyde); and hydrogen iodide in an amount of less than or equal to 0.5 wt. % (e.g., from 0.0001 to 0.5 wt. % hydrogen iodide).

The overhead stream from flasher 112 is directed to the light ends column 124 as vapor product stream 122, where distillation yields a low-boiling overhead vapor stream 126, a purified acetic acid product that preferably is removed via a side stream 128, and a high boiling residue stream 116. Acetic acid removed via side stream 128 preferably is subjected to further purification, such as in drying column 130 for selective separation of acetic acid from water. At least a portion of overhead vapor stream 126 is directed to heat exchanger 127, via line 126, where the contents of line 126 are condensed to form condensed light ends return stream 129 and light ends vent vapor stream 137. At least a portion of overhead vapor stream 126, e.g., light ends vent vapor stream 137, is directed to absorber tower 109. Condensed light ends return stream 129 is recycled to reactor 104 or optionally back to light ends column 124 (not shown).

Figure 2:
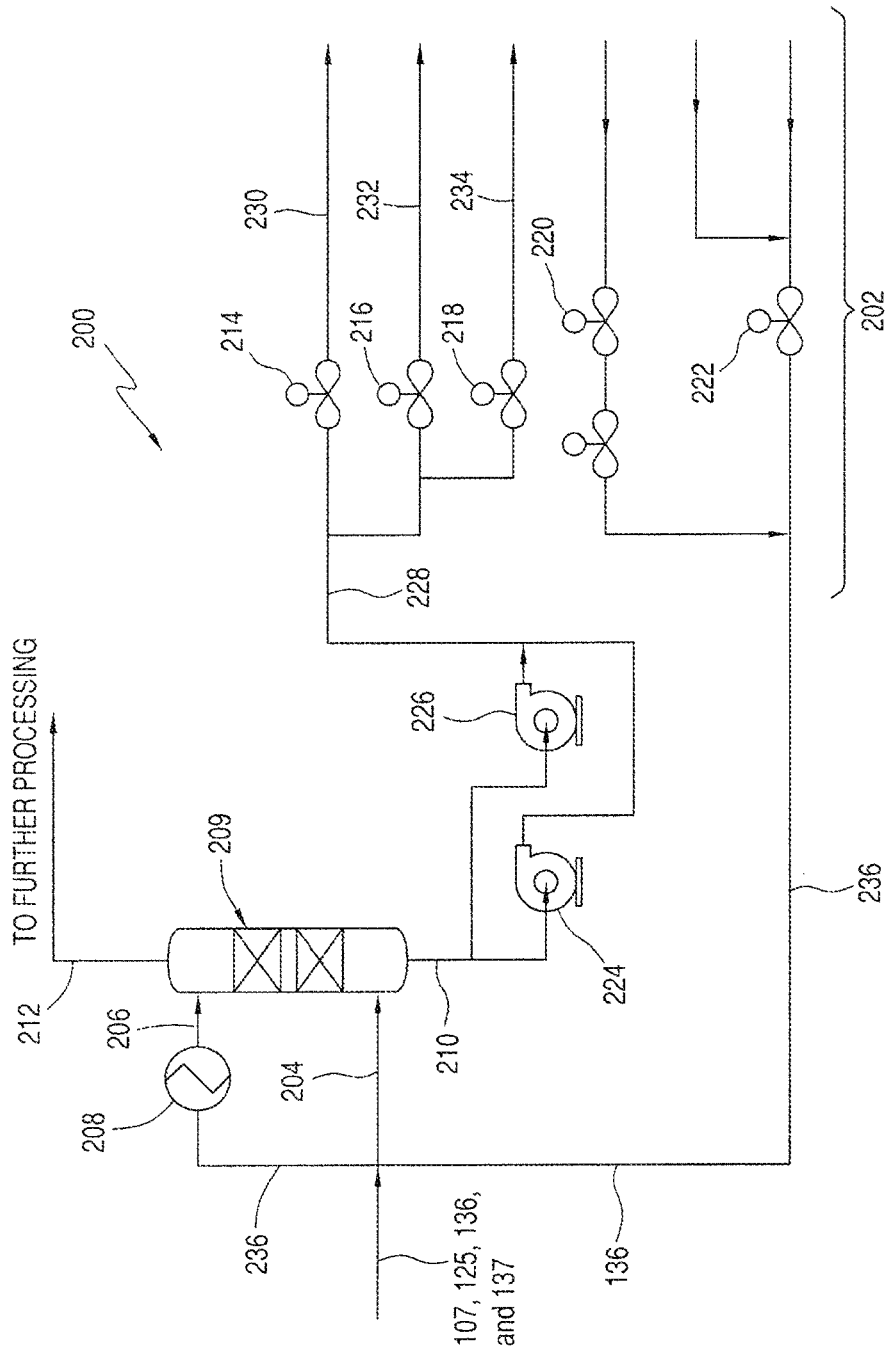
FIG. 2 shows a schematic of an absorber tower unit and the accompanying componentry in accordance with the present invention.

An exemplary absorber tower and the accompanying components are shown in FIG. 2.

One or more of streams 107, 125, 136, and 137 are directed to absorber system 200. Absorber system 200 includes switching system 202 which has a plurality of valves and pumps in order to selectively couple absorber system 200 to scrubber solvent sources and return the used extracts to the desired point in the carbonylation system as hereinafter described. Note also reactor 104 may be directly vented to absorber system 200 if necessary.

Absorber system 200 comprises absorber tower 209 which is fed with vent gas via line 204 and with scrubber solvent via line 206. Line 204 represents one or more vent streams, as shown in FIG. 1. Preferably the scrubber solvent is chilled with a chiller 208 prior to being fed to absorber tower 209 wherein the solvent flows countercurrently with respect to the vent gas, absorbing methyl iodide, hydrogen iodide, and additional relative components before exiting the tower via return line 210 and being returned to the carbonylation unit. The scrubbed vent gas exits the tower via line 212 and may be further processed. Alternatively, a second stage water scrub could be provided in absorber tower 209 if so desired. Preferably, more than 90% of the methyl iodide is removed from the vent gas. The scrubber fluid is generally chilled to a temperature from 5° C. to 25° C. prior to use in the tower, with the proviso that when acetic acid is used as the scrubber solvent, the temperature of the solvent is preferably held at 17° C., or more to prevent freezing.

Switching system 202 includes a plurality of valves such as valves 214, 216, 218, 220, 222 and one or more pumps 224, 226 to raise pressure in the return lines 228, 230, 232, 234 if needed. Feed valves 220, 222 are used to select the scrubber solvent which may be methanol from a feed tank or product acetic acid depending upon the mode of operation of absorber tower 209.

In steady state operation of the carbonylation system of FIG. 1 valve 222 is closed and methanol is fed from the feed tank through open valve 220 via line 236 to chiller 208, wherein the methanol is cooled. From the chiller, methanol is fed to absorber tower 209, where it flows countercurrently with vent gas and sorbs methyl iodide and other volatile components therefrom before exiting the column via line 210. The used solvent with sorbed methyl iodide is pumped back to the reactor or the feed tank with pumps 224, 226 via line 230. In this mode of operation valves 216, 218 are closed and valve 214 is open.

During start up or shut down of the system it may be desirable to operate absorber tower 209 using acetic acid as the scrub solvent. In this mode of operation, valve 222 is open and valve 220 is closed. Acid may be sourced from product acid or a tank if so desired. The acid flows through line 236 to chiller 208 where it is chilled and fed to absorber tower 209 via line 206 and scrubs the vent gas supplied via line 204 as noted above. The acid exits the absorber tower 209 via line 210 and is pumped back to the carbonylation system by way of pumps 224, 226 via lines 228, 232. In this mode of operation of absorber tower 209, valves 214, 218 are closed and valve 216 is open so that the used acetic acid is returned to light ends column, the drying column, or elsewhere in the purification system for stripping.

During changeover from one solvent to the other, such as from methanol to acetic acid, it is generally undesirable to return the scrub fluid to the methanol feed system or light ends column since inefficiencies result. For such, a changeover may be accomplished in from about 5 to about 20 minutes, during which time the used scrubber solvent is fed to a catalyst reservoir. In changeover mode, valves 214, 216 are closed and valve 218 is open. Thus the system is operated generally by way of (a) feeding vent gas from the carbonylation unit to the absorber tower, the vent gas including methyl iodide and optionally additional volatile components; (b) supplying a first absorbent to the absorber tower, the first absorbent consisting essentially of acetic acid; (c) contacting the vent gas with the first absorbent thereby removing methyl iodide and optionally additional volatile components from the gas and absorbing methyl iodide and optionally additional volatile components into the first absorbent; (d) feeding an absorber return stream including first absorbent and absorbed methyl iodide and optionally additional absorbed volatile components to the light ends column, the drying column or elsewhere in the purification system; (e) terminating the supply of first absorbent to the absorber tower; (f) supplying a second absorbent to the absorber tower, the second absorbent consisting essentially of methanol; (g) contacting the vent gas with the second absorbent thereby removing methyl iodide and optionally additional volatile components from the gas and absorbing methyl iodide and optionally additional volatile components into the second absorbent; (h) feeding an absorber return stream including first absorbent, second absorbent, absorbed methyl iodide and optionally additional absorbed volatile components from the absorber tower to the reactor; and (i) following the transition period, continue feeding an absorber return stream including second absorbent and absorbed methyl iodide and optionally additional absorbed volatile components to the reactor. Feed to the absorber tower is selected by operation of valves 220, 222.

Returning to the decanter operations, it has been disclosed in U.S. Pat. Nos. 6,143,930 and 6,339,171 that there is generally a higher concentration of the PRC's, and in particular acetaldehyde content, in the low-boiling overhead vapor stream exiting the light ends column than in the high-boiling residue stream exiting the column. Thus, in some cases, low-boiling overhead vapor stream 126, containing PRC's, is subjected to additional processing in PRC removal system 132 to reduce and/or remove the amount of PRC's present. As shown, low-boiling overhead vapor stream 126, therefore, is condensed and directed to an overhead phase separation unit, as shown by overhead receiver decanter 134. In addition to PRC's, low-boiling overhead vapor stream 126 may typically contain methyl iodide, methyl acetate, acetic acid, and water.

Conditions are desirably maintained in the process such that low-boiling overhead vapor stream 126, once in decanter 134, may separate to form a light phase and a heavy phase. Generally, low-boiling overhead vapor stream 126 is cooled to a temperature sufficient to condense and separate the condensable methyl iodide, methyl acetate, acetaldehyde and other carbonyl components, and water to form two separate phases. A portion of stream 126 may include noncondensable gases such as carbon monoxide, carbon dioxide, hydrogen iodide, hydrogen, and the like that can be directed to absorber tower 109.

The condensed light phase in the decanter generally may comprise water, acetic acid, and PRC's, as well as quantities of methyl iodide and methyl acetate. Hydrogen iodide may also be present in the light phase. The condensed heavy phase in decanter 134 may generally comprise methyl iodide, methyl acetate, and PRC's. Hydrogen iodide may also be present in the heavy phase. The condensed heavy liquid phase in the decanter 134 can be conveniently recirculated, either directly or indirectly, to the reactor 104 via stream 118. For example, a portion of this condensed heavy liquid phase can be recirculated to the reactor, with a slip stream (not shown), generally a small amount, e.g., from 5 to 40 vol. %, or from 5 to 20 vol. %, of the heavy liquid phase being directed to a PRS. This slip stream of the heavy liquid phase may be treated individually or may be combined with the condensed light liquid phase stream 138 for further distillation and extraction of carbonyl impurities.

Although the specific compositions of the light phase stream may vary widely, some preferred compositions are provided below in Table 1. In one embodiment, hydrogen iodide is present in the light ends overhead, preferably in an amount ranging from 0.01 wt. % to 1 wt. %, e.g., from 0.02 wt. % to 1 wt. %, or from 0.04 wt. % to 0.07 wt. %.

TABLE 1

Exemplary Light Liquid Phase from Light Ends Overhead

|  | conc. (Wt. %) | conc. (Wt. %) | conc. (Wt. %) |
|---|---|---|---|
| Water | 40-80 | 50-75 | 70-75 |
| Methyl Acetate | 1-50 | 1-25 | 1-15 |
| Acetic Acid | 1-40 | 1-25 | 5-15 |
| PRC's | <5 | <3 | <1 |
| Methyl Iodide | <10 | <5 | <3 |
| HI | <1 | <0.5 | <0.1 |

In one embodiment, the overhead decanter is arranged and constructed to maintain a low interface level to prevent an excess hold up of methyl iodide. Although the specific compositions of heavy liquid phase may vary widely, some exemplary compositions are provided below in Table 2. In one embodiment, hydrogen iodide is present in the heavy phase in addition to the components listed below.

TABLE 2

Exemplary Heavy Liquid Phase from Light Ends Overhead

|  | conc. (Wt. %) | conc. (Wt. %) | conc. (Wt. %) |
|---|---|---|---|
| Water | 0.01-2 | 0.05-1 | 0.1-0.9 |
| Methyl Acetate | 0.1-25 | 0.5-20 | 0.7-15 |
| Acetic Acid | 0.1-10 | 0.2-8 | 0.5-6 |
| PRC's | <5 | <3 | <1 |
| Methyl Iodide | 40-98 | 50-95 | 60-85 |

The density of the heavy liquid phase 134 may be from 1.3 to 2, e.g., from 1.5 to 1.8, from 1.5 to 1.75 or from 1.55 to 1.7. As described in U.S. Pat. No. 6,677,480, the measured density in the heavy liquid phase 134 correlates with the methyl acetate concentration in the reaction medium. As density decreases, the methyl acetate concentration in the reaction medium increases. In one embodiment of the present invention, heavy liquid phase 134 is recycled to the reactor and the light liquid phase 133 is controlled to be recycled through the same pump. It may be desirable to recycle a portion of the light liquid phase 133 that does not disrupt the pump and maintains a density of the combined light liquid phase 133 and heavy liquid phase of greater than or equal to 1.3, e.g., greater than or equal to 1.4, greater than or equal to 1.5, or greater than or equal to 1.7. As described herein, a portion of the heavy liquid phase 134 may be treated to remove impurities such as acetaldehyde.

As shown in FIG. 1, the light phase exits decanter 134 via stream 131. A first portion, e.g., aliquot portion, of light phase stream 131 is recycled to the top of the light ends column 124 as reflux stream 140. A second portion, e.g., aliquot portion, of light phase stream 131 is directed to PRS 132, as discussed below and as shown by stream 142. A third portion, e.g., aliquot portion, of the light phase stream 131 optionally may be recycled to reactor 104 as shown by recycle stream 114, when additional water is desired or needed in reactor 104. In preferred aspects the water level is maintained in the reactor at a desired level without recycling stream 114 to reactor 104 since recycling stream 114 to the reactor undesirably may result in the recycle of acetic acid and unnecessarily increasing the load on reactor 104. Thus, a recycle from decanter 134 to reactor 104 is through the heavy phase stream 118.

Light ends column 124 also preferably forms residuum or bottoms stream 116, which comprises primarily acetic acid and water. Since light ends bottoms stream 116 typically may comprise some residual catalyst, it may be beneficial to recycle all or a portion of light ends bottoms stream 116 to reactor 104. Optionally, light ends bottoms stream 116 may be combined with the catalyst phase 110 from flasher 112 and returned together to reactor 104, as shown in FIG. 1.

As indicated above, in addition to the overhead phase, the light ends column 124 also forms an acetic acid side stream 128, which preferably comprises primarily acetic acid and water. In order to maintain an efficient product separation, it is important that the composition of the side stream 128 does not vary or fluctuate significantly during normal operation.

Optionally, a portion of the side stream 128 may be recirculated to the light ends column, preferably to a point below where side stream 128 was removed from light ends column, in order to improve the separation.

Since side stream 128 contains water in addition to acetic acid, side stream 128 from the light ends column 124 preferably is directed to drying column 130, in which the acetic acid and water are separated from one another. As shown, drying column 130, separates acetic acid side stream 128 to form overhead stream 144 comprised primarily of water and bottoms stream 146 comprised primarily of acetic acid. Overhead stream 144 preferably is cooled and condensed in a phase separation unit, e.g., decanter 148, to form a light phase and a heavy phase. As shown, a portion of the light phase is refluxed, as shown by streams 150 and 152 and the remainder of the light phase is returned to the reactor 104, as shown by stream 120. The heavy phase, which typically is an emulsion comprising water and methyl iodide, preferably is returned in its entirety to the reactor 104, as shown by stream 122, optionally after being combined with stream 120. Exemplary compositions for the light phase of the drying column overhead are provided below in Table 3. In one embodiment, hydrogen iodide is present in the drying column overhead in an amount ranging from 0.01 wt. % to 1 wt. %, e.g., from 0.05 wt. % to 1 wt. %, or from 0.01 wt. % to 0.5 wt. %.

TABLE 3

Exemplary Light Compositions from Drying Column Overhead

|  | conc. (Wt. %) | conc. (Wt. %) | conc. (Wt. %) |
|---|---|---|---|
| HOAc | 1-20 | 1-15 | 1-10 |
| Water | 50-90 | 60-90 | 70-90 |
| MeI | <10 | <5 | <3 |
| MeAc | 1-20 | 1-15 | 1-10 |
| HI | <1 | <0.5 | <0.2 |

Drying column bottoms stream 146 preferably comprises or consists essentially of acetic acid. In preferred embodiments, drying column bottoms stream 146 comprises acetic acid in an amount greater than 90 wt. %, e.g., greater than 95 wt. % or greater than 98 wt. %. Optionally, drying column bottoms stream 146 may be further processed, e.g., by passing through an ion exchange resin, prior to being stored or transported for commercial use.

PRC Removal

In some cases, it may be advantageous to remove PRCs, primarily aldehydes such as acetaldehyde, from a low-boiling overhead vapor stream of a light ends distillation column, more preferably from the condensed light phase of a low-boiling overhead vapor stream 126 from light ends distillation column 124. One or more of the streams from PRC removal system 132 may be returned to the system, e.g., recycled, either directly or indirectly. In some cases, no return streams from the PRC removal system 132 are directed to the reactor 104 or to recycle lines to reactor 104. The PRC removal system preferably includes at least one distillation column and at least one extraction column to reduce and/or remove PRCs. US Patent Publication No. 2011/0288333, which is hereby incorporated by reference, describes various PRC removal system embodiments that may be employed with the present process.

The PRC removal system shown in FIG. 1 may contain a single extraction step or may include multiple extraction stages, as described for example in U.S. Pat. No. 7,223,886 and optionally including multistage countercurrent extraction. According to various embodiments, one or more streams derived from either or both (i) the PRC removal system distillation column and/or (ii) the PRC removal system extraction stage (collectively shown as stream 154), for example, may be returned to the system, e.g., either or both (i) the light ends removal column and/or (ii) the drying column of the separation system for the acetic acid production system. For example, a first portion, e.g., an aliquot portion, of a bottoms stream from a PRC removal system column may be directed to light ends column 124 for further processing, or a second portion, e.g., an aliquot portion, of a bottoms stream from a PRC removal system column may be directed to drying column 130, preferably the upper portion of drying column 130, for further processing. As another example, a raffinate from a PRS extraction unit, notably containing methyl iodide, may be returned to the system, e.g., light ends column or drying column or the raffinate may be added directly to decanter 134 and/or may be returned to reactor 104.

PRC Removal System

In some embodiments, a portion of light liquid phase and/or heavy liquid phase may be separated and directed to PRS to recover methyl iodide and methyl acetate during the acetaldehyde removal. As shown in Tables 1 and 2 above, light liquid phase and/or heavy liquid phase each contain PRC's and the process may include removing carbonyl impurities, such as acetaldehyde, that deteriorate the quality of the acetic acid product and may be removed in suitable impurity removal columns and absorbers as described in U.S. Pat. Nos. 6,143,930; 6,339,171; 7,223,883; 7,223,886; 7,855,306; 7,884,237; 8,889,904; and US Pub. Nos. 2006/0011462, which are incorporated herein by reference in their entirety. Carbonyl impurities, such as acetaldehyde, may react with iodide catalyst promoters to form alkyl iodides, e.g., ethyl iodide, propyl iodide, butyl iodide, pentyl iodide, hexyl iodide, etc. Also, because many impurities originate with acetaldehyde, it is desirable to remove carbonyl impurities from the liquid light phase.

The portion of light liquid phase and/or heavy liquid phase fed to the acetaldehyde or PRC removal system may vary from 1% to 99% of the mass flow of either the light liquid phase 133 and/or heavy liquid phase 134, e.g., from 1 to 50%, from 2 to 45%, from 5 to 40%, 5 to 30% or 5 to 20%. Also in some embodiments, a portion of both the light liquid phase 133 and heavy liquid phase 134 may be fed to the acetaldehyde or PRC removal system. The portion of the light liquid phase 133 not fed to the acetaldehyde or PRC removal system may be refluxed to the first column or recycled to the reactor, as described herein. The portion of the heavy liquid phase 134 not fed to the acetaldehyde or PRC removal system may be recycled to the reactor. Although a portion of heavy liquid phase 134 may be refluxed to the first column, it is more desirable to return the methyl iodide enriched heavy liquid phase 134 to the reactor.

In one embodiment at least a portion the light phase and/or the heavy phase is conveyed to the PRC removal system for separation to form an overhead comprising hydrogen iodide. In one embodiment, the PRC removal system is a one column system. In such cases, the inventors have now found that the overhead exiting the one column may contain hydrogen iodide, e.g., an enhanced amount of hydrogen iodide due to the reaction that occurs in PRC removal system via hydrolysis of methyl iodide (and/or via the reaction of methyl iodide and acetic acid to yield hydrogen iodide and methyl acetate). This stream may be sent to the absorber tower for treatment of the hydrogen iodide.

Figure 3:
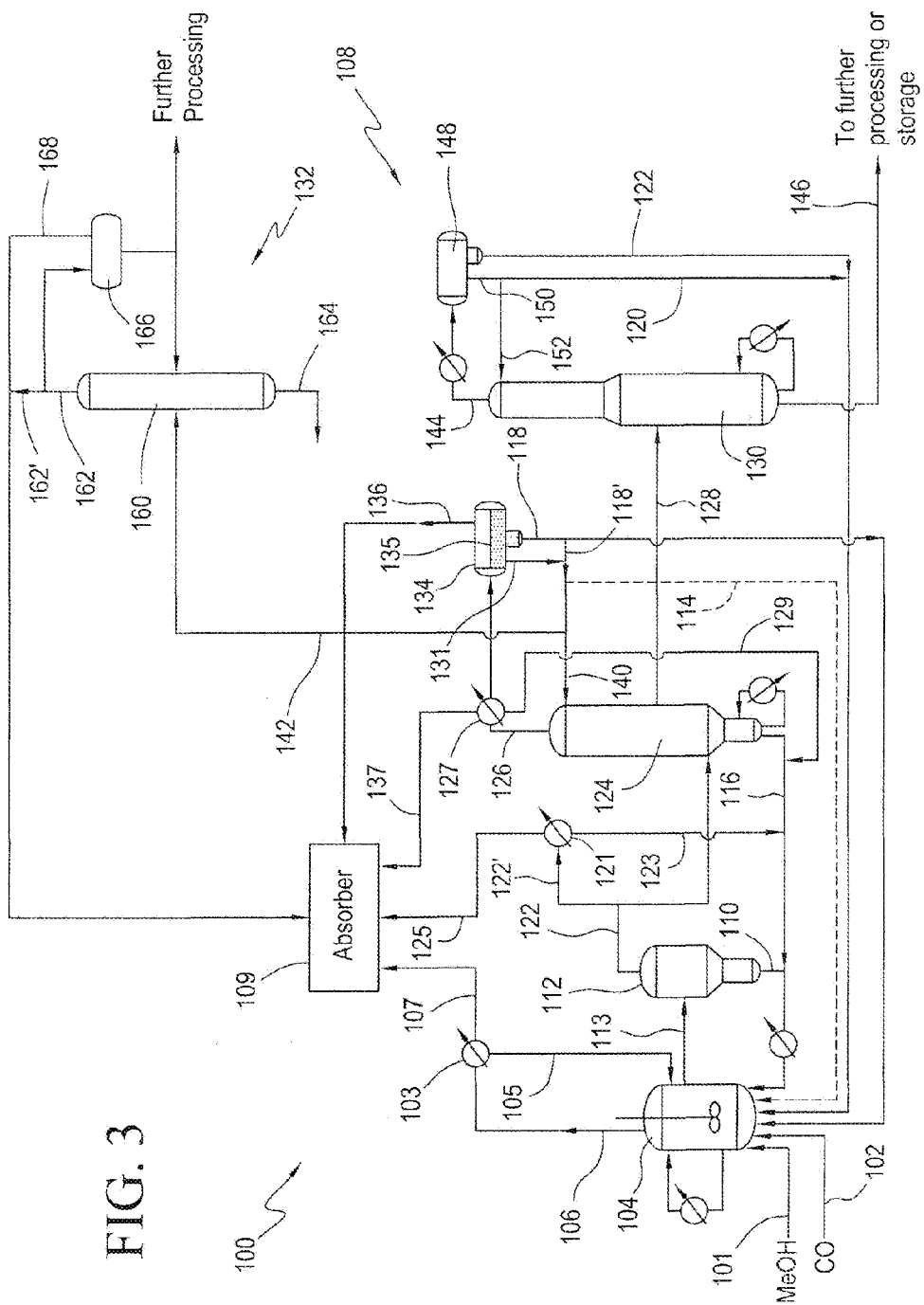
FIG. 3 shows a schematic of an acetic acid production process in accordance with the present invention.

As shown in FIG. 3, at least a portion of the light phase in line 142 and/or the heavy phase in line 118' may be directed to PRC removal system 132, which comprises column 160. Column 10 forms vapor overhead 162 and bottom process stream 164 comprising water, methyl acetate, and/or methanol. Vapor overhead 162 comprises hydrogen iodide, e.g., hydrogen iodide formed via reactions that take place in column 160. Vapor overhead 162 may be passed through a heat exchanger/condenser (not shown) and collected in receiver 166. Receiver vent 168 comprises some of the hydrogen iodide in vapor overhead 162 and is drawn from receiver 166 and conveyed to absorber 109. A portion of vapor overhead 162 may be combined with receiver vent 18 and directed to absorber 109 via line 162'. Optionally, line 162' may be conveyed directly to absorber 109 without being combined with line 168. A portion of the condensed vapor overhead stream may be returned to column 160 via and another portion may be directed to further processing.

In other embodiments, the PRS system is a two column system. The inventors have now found that the overhead exiting either column may contain hydrogen iodide, e.g., an enhanced amount of hydrogen iodide.

In one embodiment, a portion of light liquid phase 133 and/or heavy liquid phase 134 is fed to a distillation column which enriches the overhead thereof to have acetaldehyde and methyl iodide. In addition, the overhead may also be enriched in hydrogen iodide. Depending on the configuration, there may be two separate distillation columns, and the overhead of the second column may be enriched in acetaldehyde and methyl iodide. The overhead of the second may also be enriched in hydrogen iodide. Dimethyl ether, which may be formed in-situ, may also be present in the overhead. The overhead may be subject to one or more extraction stages to remove a raffinate enriched in methyl iodide and an extractant. In some cases, the overhead(s) of the PRC removal system may be treated remove carbon monoxide. As one example, a pressure swing absorber may be employed. A portion of the raffinate may be returned to the distillation column, first column, overhead decanter and/or reactor. For example, when the heavy liquid phase is treated in the PRC removal system, it may be desirable to return a portion the raffinate to either the distillation column or reactor. Also, for example, when light liquid phase 133 is treated in the PRC removal system, it may be desirable to return a portion the raffinate to either the first column, overhead decanter, or reactor. In some embodiments, the extractant may be further distilled to remove water, which is returned to the one or more extraction stages. The column bottoms, which contains more methyl acetate and methyl iodide than light liquid phase 133, may also be recycled to reactor 105 and/or refluxed to first column 120.

The overhead of a one column PRC removal unit may contain hydrogen iodide. The overhead may be collected in a receiver and a vent may be drawn from the receiver.

In one embodiment, the process of the present invention comprises the steps of: feeding to the absorber tower an absorber tower feed comprising at least a portion of the PRS overhead receiver vent stream and/or the PRS overhead (from the first and only column); and contacting the absorber tower feed with a first absorbent selected from the group consisting of acetic acid, methanol, and methyl acetate to absorb hydrogen iodide to form a first extract comprising absorbed hydrogen iodide.

In an embodiment wherein a two column system is employed, the process of the present invention comprises the steps of: feeding to an absorber tower an absorber tower feed comprising at least a portion of the PRS overhead receiver vent stream and/or the PRS overhead (from the second column); contacting the absorber tower feed with a first absorbent selected from the group consisting of acetic acid, methanol, and methyl acetate to absorb hydrogen iodide to form a first extract comprising absorbed hydrogen iodide.

In the embodiments where the overhead or receiver vent from the PRC removal system is contacted with an absorbent, the inventors have found that the treatment with absorbent efficiently removes the hydrogen iodide that may be formed in the PRC removal system.

For purposes of the present specification and claims, the overhead streams and overhead decanters of the light ends removal column and the drying column are considered to be part of the light ends removal column and of the drying column.

As indicated above, either phase of the low-boiling overhead vapor stream 126 may be subsequently processed to remove PRCs.

The distillation columns of the present invention may be a conventional distillation column, e.g., a plate column, a packed column, and others. Plate columns may include a perforated plate column, bubble-cap column, Kittel tray column, uniflux tray, or a ripple tray column. For a plate column, the theoretical number of plates is not particularly limited and depending on the species of the component to be separate, may include up to 80 plates, e.g., from 2 to 80, from 5 to 60, from 5 to 50, or more preferably from 7 to 35. The distillation column may include a combination of different distillation apparatuses. For example, a combination of bubble-cap column and perforated plate column may be used as well as a combination of perforated plate column and a packed column.

The distillation temperature and pressure in the distillation system can suitably be selected depending on the condition such as the species of the objective carboxylic acid and the species of the distillation column, or the removal target selected from the lower boiling point impurity and the higher boiling point impurity according to the composition of the feed stream. For example, in a case where the purification of acetic acid is carried out by the distillation column, the inner pressure of the distillation column (usually, the pressure of the column top) may be from 0.01 to 1 MPa, e.g., from 0.02 to 0.7 MPa, and more preferably from 0.05 to 0.5 MPa in terms of gauge pressure. Moreover, the distillation temperature for the distillation column, namely the inner temperature of the column at the temperature of the column top, can be controlled by adjusting the inner pressure of the column, and, for example, may be from 20 to 200° C., e.g., from 50 to 180° C., and more preferably from 100 to 160° C.

The material of each member or unit associated with the distillation system, including the columns, valves, condensers, receivers, pumps, reboilers, and internals, and various lines, each communicating to the distillation system may be suitable material such as glass, metal, ceramic, or combinations thereof, and is not particularly limited to a specific one. According to the present invention, the material of the foregoing distillation system and various lines are a transition metal or a transition-metal-based alloy such as iron alloy, e.g., a stainless steel, nickel or nickel alloy, zirconium or zirconium alloy thereof, titanium or titanium alloy thereof, or aluminum alloy. Suitable iron-based alloys include those containing iron as a main component, e.g., a stainless steel that also comprises chromium, nickel, molybdenum and others. Suitable nickel-based alloys include those containing nickel as a main component and one or more of chromium, iron, cobalt, molybdenum, tungsten, manganese, and others, e.g., HASTELLOY™ and INCONEL™. Corrosion-resistant metals may be particularly suitable as materials for the distillation system and various lines.

For purposes of the present specification, it should be understood that the term "aliquot portion" refers to both: (i) a portion of a parent stream that has the same composition as the parent stream from which it is derived, and (ii) a stream comprising a portion of a parent stream that has the same composition as the parent stream from which it is derived and one or more additional streams that have been combined therewith. Thus, directing a return stream comprising an aliquot portion of a PRS distillation bottoms stream to the light ends column encompasses the direct transfer of a portion of the PRS distillation bottoms stream to the light ends column as well as the transfer of a derivative stream comprising (i) a portion of the PRS distillation bottoms stream and (ii) one or more additional streams that are combined therewith prior to introduction into the light ends column. An "aliquot portion" would not include, for example, streams formed in a distillation step or a phase separation step, which would not be compositionally the same as the parent stream from which they are derived nor derived from such a stream.

One of ordinary skill in the art having the benefit of this disclosure can design and operate a PRS distillation column to achieve the desired results. Accordingly, the practice of this process is not necessarily limited to specific characteristic of a particular distillation column or the operation characteristics thereof, such as the total number of stages, the feed point, reflux ratio, feed temperature, reflux temperature, column temperature profile, and the like.

As is evident from the figures and text presented above, a variety of embodiments are contemplated:

E1. A process for producing acetic acid comprising:
carbonylating, in a reactor, at least one of methanol, dimethyl ether, and methyl acetate in a reaction medium comprising a metal catalyst, methyl iodide, an iodide salt, and optionally acetic acid and a finite amount water, to form a crude acetic acid product comprising acetic acid, optionally venting from the reactor a reactor vent stream comprising hydrogen iodide;

flashing the crude acetic acid product, with or without heat, to form a first vapor stream comprising acetic acid and methyl iodide and a first liquid residue stream comprising metal catalyst and halide salt, optionally condensing a portion of the first vapor stream to form a condensed flasher return stream and a flasher vent stream comprising hydrogen iodide;

separating, in a light ends column, the flashed first vapor stream to form a second vapor stream comprising methyl iodide and hydrogen iodide, a side draw comprising purified acetic acid product, and a second liquid residue stream;

feeding to an absorber tower an absorber tower feed comprising at least a portion of at least one of the reactor vent stream, the flasher vent stream, and the second vapor stream;

contacting the absorber tower feed with a first absorbent comprising acetic acid to absorb methyl iodide and to form a first extract comprising the first absorbent and the absorbed methyl iodide;

conveying the first extract, directly or indirectly, to the light ends column and/or drying column;

terminating the supply of first absorbent to the absorber tower;

contacting the absorber tower feed with a second absorbent comprising methanol and/or methyl acetate to absorb methyl iodide and hydrogen iodide and to form a second extract comprising the second absorbent and the absorbed methyl iodide;

conveying the second extract, directly or indirectly, to the reactor.

E2. The process according to embodiment E1, wherein the second absorbent consists essentially of methanol.

E3. The process according to embodiment E1 or E2, further comprising the step of chilling the first absorbent prior to the contacting.

E4. The process according to any one of embodiments E1 to E3, further comprising the step of chilling the second absorbent prior to the contacting.

E5. The process according to any one of embodiments E1 to E4, further comprising mixing the second absorber return stream with methanol or a reactive derivative thereof prior to the conveying.

E6. The process according to any one of embodiments E1 to E5, wherein the absorber tower feed comprises methyl acetate and the first and second absorbents absorb methyl acetate from the absorber tower feed.

E7. The process according to any one of embodiments E1 to E6, wherein the process does not employ a stripper column to treat the first absorbent and/or the second absorbent.

E8. The process according to any one of embodiments E1 to E7, wherein the carbonylating is conducted while maintaining the reaction system at concentrations of 2 to 25% by weight iodide salt, 1 to 20% by weight methyl iodide, 0.1 to 30% by weight methyl acetate, and 0.1 to 10% by weight water.

E9. The process according to any one of embodiments E1 to E8, wherein the second absorber return stream is not returned to the separation zone.

E10. The process according to any one of embodiments E1 to E9, wherein the contacting of the absorber tower feed with the methanol or methyl acetate in the second absorbent forms methyl iodide.

E11. The process according to any one of embodiments E1 to E10, wherein the conveying of the second absorber return stream comprises: conveying the second absorber return stream to the reactor during a transition period; and following the transition period, continuing to feed the second absorber return stream to the reactor.

E12. The process according to any one of embodiments E1 to E11, wherein the conveying of the second absorber return stream comprises conveying the second absorber return stream to the reactor after the termination of the supply of first absorbent.

E13. The process according to any one of embodiments E1 to E12, wherein the second vapor stream further comprises volatile components.

E14. The process according to any one of embodiments E1 to E13, wherein the flashing comprises condensing at least a portion of the first vapor stream to form the condensed flasher return stream and the flasher vent vapor stream comprising hydrogen iodide and directing the flasher vent vapor stream to the absorber tower.

E15. The process according to any one of embodiments E1 to E14, wherein the carbonylating comprises venting a reactor vent stream comprising hydrogen iodide and directing at least a portion of the reactor vent stream to the absorber tower.

E16. The process according to any one of embodiments E1 to E15, wherein the carbonylating comprises condensing at least a portion of the reactor vent stream to form a condensed reactor return stream and a reactor vent vapor stream comprising hydrogen iodide and directing the reactor vent vapor stream to the absorber tower.

E17. The process according to any one of embodiments E1 to E16, wherein the second vapor stream is decanted to form a decanter vent stream comprising hydrogen iodide and the at least a portion of the second vapor stream comprises the decanter vent stream.

E18. The process according to any one of embodiments E1 to E16, wherein the separating further comprises condensing at least a portion of the second vapor stream to form a condensed light ends return stream and a light ends vent vapor stream comprising hydrogen iodide and directing the light ends vent vapor stream to the absorber tower.

E19. A process for operating an absorber tower in a carbonylation process, the process comprising:

carbonylating, in a reactor, at least one of methanol, dimethyl ether, and methyl acetate in a reaction medium comprising a metal catalyst, methyl iodide, an iodide salt, and optionally acetic acid and a finite amount water, to form a crude acetic acid product comprising acetic acid, optionally venting from the reactor a reactor vent stream comprising hydrogen iodide;

flashing the crude acetic acid product, with or without heat, to form a first vapor stream comprising acetic acid and methyl iodide and a first liquid residue stream comprising metal catalyst and halide salt, optionally condensing at least a portion of the first vapor stream to form a condensed flasher return stream and a flasher vent stream comprising hydrogen iodide;

separating, in a light ends column, the flashed vapor stream to form a second vapor stream comprising methyl iodide and hydrogen iodide, a side draw comprising purified acetic acid product, and a second liquid residue stream;

feeding to an absorber tower at least a portion of at least one of the reactor vent stream, the flasher vent stream, and the second vapor stream to initiate a start-up period, during the start-up period, contacting the absorber tower feed with a first absorbent comprising acetic acid to absorb methyl iodide and to form a first absorber return stream comprising the first absorbent and the absorbed methyl iodide;

conveying the first absorber return stream to the light ends column and/or drying column;

transitioning from start up to steady operation during a changeover period by terminating the supply of first absorbent to the absorber tower;

providing to the absorber tower a second absorbent comprising methanol and/or methyl acetate, wherein, during at least a portion of the changeover period, acetic acid, methanol and methyl iodide are provided to the absorber tower;

forming a combined absorber return stream comprising acetic acid, methanol, and methyl iodide;

conveying the combined absorber return stream from the absorber tower to the reactor initiating steady state operation after the changeover period, during steady state operation, contacting the second vapor stream with a second absorbent comprising methanol and/or methyl acetate to absorb methyl iodide and hydrogen iodide and to form a second absorber return stream comprising the second absorbent and the absorbed methyl iodide;

during the steady state operation, mixing the second absorber return stream with methanol or a reactive derivative thereof to form a mixed stream; and conveying the mixed stream to the reactor.

E20. The process according to embodiment E19, wherein the second absorbent consists essentially of methanol.

E21. The process according to embodiment E19 or E20, further comprising the step of chilling the first absorbent and/or the second absorbent prior to the contacting.

E22. The process according to any one of embodiments E19 to E21, wherein termination of supply of first absorbent to the absorber tower and providing of the second absorbent to the absorber tower occur substantially simultaneously.

E23. The process according to any one of embodiments E19 to E22, wherein at least a portion of at least two of the reactor vent stream, the flasher vent stream, and the second vapor stream are combined to form the absorber tower feed.

E24. The process according to any one of embodiments E19 to E23, wherein the flow rate of the reactor vent stream and the second vapor stream are greater than the combined flow rate of the remaining vent streams.

E25. A process for producing acetic acid, the process comprising:

carbonylating, in a reactor, at least one of methanol, dimethyl ether, and methyl acetate in a reaction medium comprising a metal catalyst, methyl iodide, an iodide salt, and optionally acetic acid and a finite amount water, to form a crude acetic acid product comprising acetic acid, optionally venting from the reactor a reactor vent stream comprising hydrogen iodide;

condensing at least a portion of the reactor vent stream to form a condensed reactor vent stream;

feeding to an absorber tower an absorber tower feed comprising at least a portion of the condensed reactor vent stream;

contacting the absorber tower feed with a first absorbent selected from the group consisting of acetic acid, methanol, and methyl acetate to absorb methyl iodide and hydrogen iodide and to form a first extract comprising the first absorbent and the absorbed methyl iodide and hydrogen iodide;

conveying the first extract, directly or indirectly, to the light ends column and/or drying column;

decreasing the supply of first absorbent to the absorber tower;

contacting the absorber tower feed with a second absorbent comprising methanol and/or methyl acetate to absorb methyl iodide and hydrogen iodide and to form a second extract comprising the second absorbent and the absorbed methyl iodide;

conveying the second extract, directly or indirectly, to the reactor.

E26. A process for producing acetic acid, the process comprising:

carbonylating, in a reactor, at least one of methanol, dimethyl ether, and methyl acetate in a reaction medium comprising a metal catalyst, methyl iodide, an iodide salt, and optionally acetic acid and a finite amount water, to form a crude acetic acid product comprising acetic acid;

flashing the crude acetic acid product, with or without heat, to form a first vapor stream comprising acetic acid and methyl iodide and a first liquid residue stream comprising metal catalyst and halide salt, optionally condensing a portion of the first vapor stream to form a condensed flasher return stream and a flasher vent stream comprising hydrogen iodide;

feeding to an absorber tower an absorber tower feed comprising at least a portion of the flasher vent stream;

contacting the absorber tower feed with a first absorbent selected from the group consisting of acetic acid, methanol, and methyl acetate to absorb methyl iodide and hydrogen iodide and to form a first extract comprising the first absorbent and the absorbed methyl iodide and hydrogen iodide;

conveying the first extract, directly or indirectly, to the light ends column and/or drying column;

decreasing the supply of first absorbent to the absorber tower;

contacting the absorber tower feed with a second absorbent comprising methanol and/or methyl acetate to absorb methyl iodide and hydrogen iodide and to form a second extract comprising the second absorbent and the absorbed methyl iodide;

conveying the second extract, directly or indirectly, to the reactor.

E27. The process according to embodiment E26, wherein the flasher vent stream is condensed prior to the feeding step.

E28. A process for producing acetic acid, the process comprising:

carbonylating, in a reactor, at least one of methanol, dimethyl ether, and methyl acetate in a reaction medium comprising a metal catalyst, methyl iodide, an iodide salt, and optionally acetic acid and a finite amount water, to form a crude acetic acid product comprising acetic acid;

flashing the crude acetic acid product, with or without heat, to form a first vapor stream comprising acetic acid and methyl iodide and a first liquid residue stream comprising metal catalyst and halide salt;

separating, in a light ends column, the flashed first vapor stream to form a second vapor stream comprising methyl iodide and hydrogen iodide, a side draw comprising purified acetic acid product, and a second liquid residue stream;

feeding to an absorber tower an absorber tower feed comprising at least a portion of the second vapor stream;

contacting the absorber tower feed with a first absorbent selected from the group consisting of acetic acid, methanol, and methyl acetate to absorb methyl iodide and hydrogen iodide and to form a first extract comprising the first absorbent and the absorbed methyl iodide and hydrogen iodide;

conveying the first extract, directly or indirectly, to the light ends column and/or drying column;

decreasing the supply of first absorbent to the absorber tower;

contacting the absorber tower feed with a second absorbent comprising methanol and/or methyl acetate to absorb methyl iodide and hydrogen iodide and to form a second extract comprising the second absorbent and the absorbed methyl iodide;

conveying the second extract, directly or indirectly, to the reactor.

E29. The process according to embodiment E28, wherein the second vapor stream is condensed prior to the feeding step.

E30. A process for producing acetic acid, the process comprising:

carbonylating, in a reactor, at least one of methanol, dimethyl ether, and methyl acetate in a reaction medium comprising a metal catalyst, methyl iodide, an iodide salt, and optionally acetic acid and a finite amount water, to form a crude acetic acid product comprising acetic acid;

flashing the crude acetic acid product, with or without heat, to form a first vapor stream comprising acetic acid and methyl iodide and a first liquid residue stream comprising metal catalyst and halide salt, optionally condensing a portion of the first vapor stream to form a condensed flasher return stream and a flasher vent stream comprising hydrogen iodide;

separating, in a light ends column, the flashed first vapor stream to form a second vapor stream comprising methyl iodide and hydrogen iodide, a side draw comprising purified acetic acid product, and a second liquid residue stream;

decanting the second vapor stream to form a light phase comprising acetaldehyde and hydrogen iodide and a heavy phase comprising acetaldehyde, methyl iodide, methyl acetate, and hydrogen iodide;

separating at least a portion of the light phase and/or the heavy phase in a PRC removal system to form a PRS overhead comprising hydrogen iodide;

optionally collecting the PRS overhead in an overhead receiver and venting from the overhead receiver a PRS overhead receiver vent stream comprising hydrogen iodide;

feeding to an absorber tower an absorber tower feed comprising at least a portion of the PRS overhead receiver vent stream and/or the PRS overhead;

contacting the absorber tower feed with a first absorbent selected from the group consisting of acetic acid, methanol, and methyl acetate to absorb hydrogen iodide to form a first extract comprising absorbed hydrogen iodide.

E31. A process for producing acetic acid, the process comprising:

carbonylating, in a reactor, at least one of methanol, dimethyl ether, and methyl acetate in a reaction medium comprising a metal catalyst, methyl iodide, an iodide salt, and optionally acetic acid and a finite amount water, to form a crude acetic acid product comprising acetic acid, optionally venting from the reactor a reactor vent stream comprising hydrogen iodide;

flashing the crude acetic acid product, with or without heat, to form a first vapor stream comprising acetic acid and methyl iodide and a first liquid residue stream comprising metal catalyst and halide salt, optionally condensing a portion of the first vapor stream to form a condensed flasher return stream and a flasher vent stream comprising hydrogen iodide;

separating, in a light ends column, the flashed first vapor stream to form a second vapor stream comprising methyl iodide and hydrogen iodide, a side draw comprising purified acetic acid product, and a second liquid residue stream;

decanting the second vapor stream to form a light phase comprising acetaldehyde and hydrogen iodide and a heavy phase comprising acetaldehyde, methyl iodide, methyl acetate, and hydrogen iodide separating at least a portion of the light phase and/or the heavy phase to a PRC removal system to form a PRS overhead comprising hydrogen iodide;

optionally collecting the PRS overhead in an overhead receiver and venting from the overhead receiver a PRS overhead receiver vent stream comprising hydrogen iodide;

feeding to an absorber tower an absorber tower feed comprising at least a portion of the PRS overhead receiver vent stream and/or the PRS overhead;

contacting the absorber tower feed with a first absorbent selected from the group consisting of acetic acid, methanol, and methyl acetate to absorb methyl iodide and hydrogen iodide to form a first extract comprising the first absorbent and the absorbed methyl iodide and hydrogen iodide;

decreasing the supply of first absorbent to the absorber tower;

contacting the absorber tower feed with a second absorbent comprising methanol and/or methyl acetate to absorb methyl iodide and hydrogen iodide and to form a second extract comprising the second absorbent and the absorbed methyl iodide.

E32. The process according to embodiment E31, further comprising conveying the second extract, directly or indirectly, to the reactor.

E33. A process for producing acetic acid, the process comprising:

carbonylating, in a reactor, at least one of methanol, dimethyl ether, and methyl acetate in a reaction medium comprising a metal catalyst, methyl iodide, an iodide salt, and optionally acetic acid and a finite amount water, to form a crude acetic acid product comprising acetic acid;

flashing the crude acetic acid product, with or without heat, to form a first vapor stream comprising acetic acid and methyl iodide and a first liquid residue stream comprising metal catalyst and halide salt, optionally condensing a portion of the first vapor stream to form a condensed flasher return stream and a flasher vent stream comprising hydrogen iodide;

feeding to an absorber tower an absorber tower feed comprising at least a portion of the flasher vent stream;

contacting the absorber tower feed with a first absorbent selected from the group consisting of acetic acid, methanol, and methyl acetate to absorb methyl iodide and hydrogen iodide to form a first extract comprising the first absorbent, hydrogen iodide, and methyl iodide.

E34. A process for producing acetic acid, the process comprising:

carbonylating, in a reactor, at least one of methanol, dimethyl ether, and methyl acetate in a reaction medium comprising a metal catalyst, methyl iodide, an iodide salt, and optionally acetic acid and a finite amount water, to form a crude acetic acid product comprising acetic acid;

flashing the crude acetic acid product, with or without heat, to form a first vapor stream comprising acetic acid and methyl iodide and a first liquid residue stream comprising metal catalyst and halide salt;

separating, in a light ends column, the flashed first vapor stream to form a second vapor stream comprising methyl iodide and hydrogen iodide, a side draw comprising purified acetic acid product, and a second liquid residue stream;

feeding to an absorber tower an absorber tower feed comprising at least a portion of the second vapor stream;

contacting the absorber tower feed with a first absorbent selected from the group consisting of acetic acid, methanol, and methyl acetate to absorb methyl iodide and hydrogen iodide to form a first extract comprising the first absorbent, hydrogen iodide, and methyl iodide.

E35. A process for producing acetic acid, the process comprising:

carbonylating, in a reactor, at least one of methanol, dimethyl ether, and methyl acetate in a reaction medium comprising a metal catalyst, methyl iodide, an iodide salt, and optionally acetic acid and a finite amount water, to form a crude acetic acid product comprising acetic acid;

flashing the crude acetic acid product, with or without heat, to form a first vapor stream comprising acetic acid and methyl iodide and a first liquid residue stream comprising metal catalyst and halide salt, optionally condensing a portion of the first vapor stream to form a condensed flasher return stream and a flasher vent stream comprising hydrogen iodide;

separating, in a light ends column, the flashed first vapor stream to form a second vapor stream comprising methyl iodide and hydrogen iodide, a side draw comprising purified acetic acid product, and a second liquid residue stream;

decanting the second vapor stream to form a light phase comprising acetaldehyde and hydrogen iodide and a heavy phase comprising acetaldehyde, methyl iodide, methyl acetate, and hydrogen iodide;

separating at least a portion of the light phase and/or the heavy phase in a PRC removal system comprising a single column to form a PRS overhead comprising hydrogen iodide;

optionally collecting the PRS overhead in an overhead receiver and venting from the overhead receiver a PRS overhead receiver vent stream comprising hydrogen iodide;

feeding to an absorber tower an absorber tower feed comprising at least a portion of the PRS overhead receiver vent stream and/or the PRS overhead;

contacting the absorber tower feed with a first absorbent selected from the group consisting of acetic acid, methanol, and methyl acetate to absorb hydrogen iodide to form a first extract comprising absorbed hydrogen iodide; and optionally contacting the absorber tower feed with a second absorbent comprising methanol and/or methyl acetate to absorb methyl iodide and hydrogen iodide and to form a second extract comprising the second absorbent and the absorbed methyl iodide.

E36. A process for producing acetic acid, the process comprising:

carbonylating, in a reactor, at least one of methanol, dimethyl ether, and methyl acetate in a reaction medium comprising a metal catalyst, methyl iodide, an iodide salt, and optionally acetic acid and a finite amount water, to form a crude acetic acid product comprising acetic acid;

flashing the crude acetic acid product, with or without heat, to form a first vapor stream comprising acetic acid and methyl iodide and a first liquid residue stream comprising metal catalyst and halide salt, optionally condensing a portion of the first vapor stream to form a condensed flasher return stream and a flasher vent stream comprising hydrogen iodide;

separating, in a light ends column, the flashed first vapor stream to form a second vapor stream comprising methyl iodide and hydrogen iodide, a side draw comprising purified acetic acid product, and a second liquid residue stream;

decanting the second vapor stream to form a light phase comprising acetaldehyde and hydrogen iodide and a heavy phase comprising acetaldehyde, methyl iodide, methyl acetate, and hydrogen iodide;

separating at least a portion of the light phase and/or the heavy phase in a PRC removal system comprising a first column and a second column to obtain a second PRS overhead comprising hydrogen iodide from the second PRC removal column;

optionally collecting the second PRS overhead in an overhead receiver and venting from the overhead receiver a second PRS overhead receiver vent stream comprising hydrogen iodide;

feeding to an absorber tower an absorber tower feed comprising at least a portion of the second PRS overhead receiver vent stream and/or the second PRS overhead;

contacting the absorber tower feed with a first absorbent selected from the group consisting of acetic acid, methanol, and methyl acetate to absorb hydrogen iodide to form a first extract comprising absorbed hydrogen iodide; and optionally contacting the absorber tower feed with a second absorbent comprising methanol and/or methyl acetate to absorb methyl iodide and hydrogen iodide and to form a second extract comprising the second absorbent and the absorbed methyl iodide.

E37. The process according to any one of embodiments E1 to E36, wherein the second absorbent consists essentially of methanol.

E38. The process according to any one of embodiments E1 to E37, further comprising the step of chilling the first absorbent or the second absorbent prior to the contacting.

E39. The process according to any one of embodiments E1 to E38, wherein the second vapor stream is condensed prior to the feeding step.

E40. The process according to any one of embodiments E1 to E39, further comprising conveying the second extract, directly or indirectly, to the reactor.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference. In addition, it should be understood that aspects of the invention and portions of various embodiments and various features recited below and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

We claim:

1. A process for producing acetic acid, the process comprising:

carbonylating, in a reactor, at least one of methanol, dimethyl ether, and methyl acetate in a reaction medium comprising a metal catalyst, methyl iodide, an iodide salt, and optionally acetic acid and a finite amount water, to form a crude acetic acid product comprising acetic acid, optionally venting from the reactor a reactor vent stream comprising hydrogen iodide;

condensing at least a portion of the reactor vent stream to form a condensed reactor vent stream;

feeding to an absorber tower an absorber tower feed comprising at least a portion of the condensed reactor vent stream;

contacting the absorber tower feed with a first absorbent selected from the group consisting of acetic acid, methanol, and methyl acetate to absorb methyl iodide and hydrogen iodide and to form a first extract comprising the first absorbent and the absorbed methyl iodide and hydrogen iodide;

conveying the first extract, directly or indirectly, to the light ends column and/or drying column;

decreasing the supply of first absorbent to the absorber tower;

contacting the absorber tower feed with a second absorbent comprising methanol and/or methyl acetate to absorb methyl iodide and hydrogen iodide and to form a second extract comprising the second absorbent and the absorbed methyl iodide;

conveying the second extract, directly or indirectly, to the reactor.

2. The process of claim 1, wherein the second absorbent consists essentially of methanol.

3. The process of claim 1, further comprising the step of chilling the first absorbent or the second absorbent prior to the contacting.

4. The process of claim 1, further comprising conveying the second extract, directly or indirectly, to the reactor.

5. A process for producing acetic acid, the process comprising:

carbonylating, in a reactor, at least one of methanol, dimethyl ether, and methyl acetate in a reaction medium comprising a metal catalyst, methyl iodide, an iodide salt, and optionally acetic acid and a finite amount water, to form a crude acetic acid product comprising acetic acid;

flashing the crude acetic acid product, with or without heat, to form a first vapor stream comprising acetic acid and methyl iodide and a first liquid residue stream comprising metal catalyst and halide salt, optionally condensing a portion of the first vapor stream to form a condensed flasher return stream and a flasher vent stream comprising hydrogen iodide;

feeding to an absorber tower an absorber tower feed comprising at least a portion of the flasher vent stream;

contacting the absorber tower feed with a first absorbent selected from the group consisting of acetic acid, methanol, and methyl acetate to absorb methyl iodide and hydrogen iodide and to form a first extract comprising the first absorbent and the absorbed methyl iodide and hydrogen iodide;

conveying the first extract, directly or indirectly, to the light ends column and/or drying column;

decreasing the supply of first absorbent to the absorber tower;

contacting the absorber tower feed with a second absorbent comprising methanol and/or methyl acetate to absorb methyl iodide and hydrogen iodide and to form a second extract comprising the second absorbent and the absorbed methyl iodide;

conveying the second extract, directly or indirectly, to the reactor.

6. The process of claim 5, wherein the second absorbent consists essentially of methanol.

7. The process of claim 5, further comprising the step of chilling the first absorbent or the second absorbent prior to the contacting.

8. The process of claim 5, wherein the flasher vent stream is condensed prior to the feeding step.

9. The process of claim 5, further comprising conveying the second extract, directly or indirectly, to the reactor.

10. A process for producing acetic acid, the process comprising:

carbonylating, in a reactor, at least one of methanol, dimethyl ether, and methyl acetate in a reaction medium comprising a metal catalyst, methyl iodide, an iodide salt, and optionally acetic acid and a finite amount water, to form a crude acetic acid product comprising acetic acid;

flashing the crude acetic acid product, with or without heat, to form a first vapor stream comprising acetic acid and methyl iodide and a first liquid residue stream comprising metal catalyst and halide salt;

separating, in a light ends column, the flashed first vapor stream to form a second vapor stream comprising methyl iodide and hydrogen iodide, a side draw comprising purified acetic acid product, and a second liquid residue stream;

feeding to an absorber tower an absorber tower feed comprising at least a portion of the second vapor stream;

contacting the absorber tower feed with a first absorbent selected from the group consisting of acetic acid, methanol, and methyl acetate to absorb methyl iodide and hydrogen iodide and to form a first extract comprising the first absorbent and the absorbed methyl iodide and hydrogen iodide;

conveying the first extract, directly or indirectly, to the light ends column and/or drying column;

decreasing the supply of first absorbent to the absorber tower;

contacting the absorber tower feed with a second absorbent comprising methanol and/or methyl acetate to absorb methyl iodide and hydrogen iodide and to form a second extract comprising the second absorbent and the absorbed methyl iodide;

conveying the second extract, directly or indirectly, to the reactor.

11. The process of claim 10, wherein the second absorbent consists essentially of methanol.

12. The process of claim 10, further comprising the step of chilling the first absorbent or the second absorbent prior to the contacting.

13. The process of claim 10, wherein the second vapor stream is condensed prior to the feeding step.

14. The process of claim 10, further comprising conveying the second extract, directly or indirectly, to the reactor.

15. A process for producing acetic acid, the process comprising:

carbonylating, in a reactor, at least one of methanol, dimethyl ether, and methyl acetate in a reaction medium comprising a metal catalyst, methyl iodide, an iodide salt, and optionally acetic acid and a finite amount water, to form a crude acetic acid product comprising acetic acid, optionally venting from the reactor a reactor vent stream comprising hydrogen iodide;

flashing the crude acetic acid product, with or without heat, to form a first vapor stream comprising acetic acid and methyl iodide and a first liquid residue stream comprising metal catalyst and halide salt, optionally condensing a portion of the first vapor stream to form a condensed flasher return stream and a flasher vent stream comprising hydrogen iodide;

separating, in a light ends column, the flashed first vapor stream to form a second vapor stream comprising methyl iodide and hydrogen iodide, a side draw comprising purified acetic acid product, and a second liquid residue stream;

decanting the second vapor stream to form a light phase comprising acetaldehyde and hydrogen iodide and a heavy phase comprising acetaldehyde, methyl iodide, methyl acetate, and hydrogen iodide separating at least a portion of the light phase and/or the heavy phase to a permanganate reducing compound removal system to form a permanganate reducing compound removal system overhead comprising hydrogen iodide;

optionally collecting the permanganate reducing compound removal system overhead in an overhead receiver and venting from the overhead receiver a permanganate reducing compound removal system overhead receiver vent stream comprising hydrogen iodide;

feeding to an absorber tower an absorber tower feed comprising at least a portion of the PRS overhead receiver vent stream and/or the permanganate reducing compound removal system overhead;

contacting the absorber tower feed with a first absorbent selected from the group consisting of acetic acid, methanol, and methyl acetate to absorb methyl iodide and hydrogen iodide to form a first extract comprising the first absorbent and the absorbed methyl iodide and hydrogen iodide;

decreasing the supply of first absorbent to the absorber tower;

contacting the absorber tower feed with a second absorbent comprising methanol and/or methyl acetate to absorb methyl iodide and hydrogen iodide and to form a second extract comprising the second absorbent and the absorbed methyl iodide.

16. The process of claim 15, wherein the second absorbent consists essentially of methanol.

17. The process of claim 15, further comprising the step of chilling the first absorbent or the second absorbent prior to the contacting.

18. The process of claim 15, wherein the second vapor stream is condensed prior to the feeding step.

19. The process of claim 15, further comprising conveying the second extract, directly or indirectly, to the reactor.

20. A process for producing acetic acid, the process comprising:

carbonylating, in a reactor, at least one of methanol, dimethyl ether, and methyl acetate in a reaction medium comprising a metal catalyst, methyl iodide, an iodide salt, and optionally acetic acid and a finite amount water, to form a crude acetic acid product comprising acetic acid;

flashing the crude acetic acid product, with or without heat, to form a first vapor stream comprising acetic acid and methyl iodide and a first liquid residue stream comprising metal catalyst and halide salt, optionally condensing a portion of the first vapor stream to form a condensed flasher return stream and a flasher vent stream comprising hydrogen iodide;

feeding to an absorber tower an absorber tower feed comprising at least a portion of the flasher vent stream;

contacting the absorber tower feed with a first absorbent selected from the group consisting of acetic acid, methanol, and methyl acetate to absorb methyl iodide and hydrogen iodide to form a first extract comprising the first absorbent, hydrogen iodide, and methyl iodide.

21. The process of claim 20, wherein the first absorbent is acetic acid.

22. A process for producing acetic acid, the process comprising:

carbonylating, in a reactor, at least one of methanol, dimethyl ether, and methyl acetate in a reaction medium comprising a metal catalyst, methyl iodide, an iodide salt, and optionally acetic acid and a finite amount water, to form a crude acetic acid product comprising acetic acid;

flashing the crude acetic acid product, with or without heat, to form a first vapor stream comprising acetic acid and methyl iodide and a first liquid residue stream comprising metal catalyst and halide salt;

separating, in a light ends column, the flashed first vapor stream to form a second vapor stream comprising methyl iodide and hydrogen iodide, a side draw comprising purified acetic acid product, and a second liquid residue stream;

feeding to an absorber tower an absorber tower feed comprising at least a portion of the second vapor stream;

contacting the absorber tower feed with a first absorbent selected from the group consisting of acetic acid, methanol, and methyl acetate to absorb methyl iodide and hydrogen iodide to form a first extract comprising the first absorbent, hydrogen iodide, and methyl iodide.

23. The process of claim 22, wherein the first absorbent is acetic acid.

24. A process for producing acetic acid, the process comprising:

carbonylating, in a reactor, at least one of methanol, dimethyl ether, and methyl acetate in a reaction medium comprising a metal catalyst, methyl iodide, an iodide salt, and optionally acetic acid and a finite amount water, to form a crude acetic acid product comprising acetic acid;

flashing the crude acetic acid product, with or without heat, to form a first vapor stream comprising acetic acid and methyl iodide and a first liquid residue stream comprising metal catalyst and halide salt, optionally condensing a portion of the first vapor stream to form a condensed flasher return stream and a flasher vent stream comprising hydrogen iodide;

separating, in a light ends column, the flashed first vapor stream to form a second vapor stream comprising methyl iodide and hydrogen iodide, a side draw comprising purified acetic acid product, and a second liquid residue stream;

decanting the second vapor stream to form a light phase comprising acetaldehyde and hydrogen iodide and a heavy phase comprising acetaldehyde, methyl iodide, methyl acetate, and hydrogen iodide;

separating at least a portion of the light phase and/or the heavy phase in a permanganate reducing compound removal system to form a permanganate reducing compound removal system overhead comprising hydrogen iodide;

optionally collecting the permanganate reducing compound removal system overhead in an overhead receiver and venting from the overhead receiver a permanganate reducing compound removal system overhead receiver vent stream comprising hydrogen iodide;

feeding to an absorber tower an absorber tower feed comprising at least a portion of the PRS overhead receiver vent stream and/or the permanganate reducing compound removal system overhead;

contacting the absorber tower feed with a first absorbent selected from the group consisting of acetic acid, methanol, and methyl acetate to absorb hydrogen iodide to form a first extract comprising absorbed hydrogen iodide.

25. The process of claim 20, wherein the first absorbent is acetic acid.

26. A process for producing acetic acid, the process comprising:

carbonylating, in a reactor, at least one of methanol, dimethyl ether, and methyl acetate in a reaction medium comprising a metal catalyst, methyl iodide, an iodide salt, and optionally acetic acid and a finite amount water, to form a crude acetic acid product comprising acetic acid;

flashing the crude acetic acid product, with or without heat, to form a first vapor stream comprising acetic acid and methyl iodide and a first liquid residue stream comprising metal catalyst and halide salt, optionally condensing a portion of the first vapor stream to form a condensed flasher return stream and a flasher vent stream comprising hydrogen iodide;

separating, in a light ends column, the flashed first vapor stream to form a second vapor stream comprising methyl iodide and hydrogen iodide, a side draw comprising purified acetic acid product, and a second liquid residue stream;

decanting the second vapor stream to form a light phase comprising acetaldehyde and hydrogen iodide and a heavy phase comprising acetaldehyde, methyl iodide, methyl acetate, and hydrogen iodide;

separating at least a portion of the light phase and/or the heavy phase in a permanganate reducing compound removal system comprising a single column to form a permanganate reducing compound removal system overhead comprising hydrogen iodide;

optionally collecting the permanganate reducing compound removal system overhead in an overhead receiver and venting from the overhead receiver a permanganate reducing compound removal system overhead receiver vent stream comprising hydrogen iodide;

feeding to an absorber tower an absorber tower feed comprising at least a portion of the permanganate reducing compound removal system overhead receiver vent stream and/or the permanganate reducing compound removal system overhead;

contacting the absorber tower feed with a first absorbent selected from the group consisting of acetic acid, methanol, and methyl acetate to absorb hydrogen iodide to form a first extract comprising absorbed hydrogen iodide; and optionally contacting the absorber tower feed with a second absorbent comprising methanol and/or methyl acetate to absorb methyl iodide and hydrogen iodide and to form a second extract comprising the second absorbent and the absorbed methyl iodide.

27. The process of claim 26, wherein the first absorbent is acetic acid.

28. A process for producing acetic acid, the process comprising:

carbonylating, in a reactor, at least one of methanol, dimethyl ether, and methyl acetate in a reaction medium comprising a metal catalyst, methyl iodide, an iodide salt, and optionally acetic acid and a finite amount water, to form a crude acetic acid product comprising acetic acid;

flashing the crude acetic acid product, with or without heat, to form a first vapor stream comprising acetic acid and methyl iodide and a first liquid residue stream comprising metal catalyst and halide salt, optionally condensing a portion of the first vapor stream to form a condensed flasher return stream and a flasher vent stream comprising hydrogen iodide;

separating, in a light ends column, the flashed first vapor stream to form a second vapor stream comprising methyl iodide and hydrogen iodide, a side draw comprising purified acetic acid product, and a second liquid residue stream;

decanting the second vapor stream to form a light phase comprising acetaldehyde and hydrogen iodide and a heavy phase comprising acetaldehyde, methyl iodide, methyl acetate, and hydrogen iodide;

separating at least a portion of the light phase and/or the heavy phase in a permanganate reducing compound removal system comprising a first column and a second column to obtain a second permanganate reducing compound removal system overhead comprising hydrogen iodide from the second permanganate reducing compound removal column;

optionally collecting the second permanganate reducing compound removal system overhead in an overhead receiver and venting from the overhead receiver a second permanganate reducing compound removal system overhead receiver vent stream comprising hydrogen iodide;

feeding to an absorber tower an absorber tower feed comprising at least a portion of the second PRS overhead receiver vent stream and/or the second permanganate reducing compound removal system overhead;

contacting the absorber tower feed with a first absorbent selected from the group consisting of acetic acid, methanol, and methyl acetate to absorb hydrogen iodide to form a first extract comprising absorbed hydrogen iodide; and optionally contacting the absorber tower feed with a second absorbent comprising methanol and/or methyl acetate to absorb methyl iodide and hydrogen iodide and to form a second extract comprising the second absorbent and the absorbed methyl iodide.

29. The process of claim 28, wherein the first absorbent is acetic acid.

* * * * *